US008722093B2

(12) United States Patent
Raghavan

(10) Patent No.: US 8,722,093 B2
(45) Date of Patent: May 13, 2014

(54) POLICOSANOL NANOPARTICLES

(75) Inventor: Palayakotai R. Raghavan, Chappaqua, NY (US)

(73) Assignee: NanoRx, Inc., Chappaqua, NY (US)

( * ) Notice: Subject to any disclaimer, the term of this patent is extended or adjusted under 35 U.S.C. 154(b) by 387 days.

(21) Appl. No.: 12/691,706

(22) Filed: Jan. 21, 2010

(65) Prior Publication Data

US 2010/0215752 A1     Aug. 26, 2010

Related U.S. Application Data

(60) Provisional application No. 61/154,712, filed on Feb. 23, 2009.

(51) Int. Cl.
*A61K 9/14* (2006.01)
*A61K 9/50* (2006.01)
*A61K 31/045* (2006.01)

(52) U.S. Cl.
USPC ............................ 424/489; 424/502; 514/724

(58) Field of Classification Search
CPC . A61K 31/045; A61K 31/075; A61K 31/192; A61K 31/194; A61K 31/219; A61K 9/14; A61K 9/1617; A61K 9/2013; A61K 9/5123
USPC ........................... 424/849, 489, 502; 514/724
See application file for complete search history.

(56) References Cited

U.S. PATENT DOCUMENTS

| 5,278,189 | A | 1/1994 | Rath et al. |
| 7,214,394 | B2 | 5/2007 | Empie et al. |
| 7,320,802 | B2 | 1/2008 | Ryde et al. |
| 7,763,278 | B2 | 7/2010 | Cooper et al. |
| 2003/0232796 | A1* | 12/2003 | Cooper et al. ............... 514/169 |
| 2005/0095297 | A1 | 5/2005 | Grenier et al. |
| 2005/0234025 | A1 | 10/2005 | Kutney et al. |
| 2005/0267091 | A1 | 12/2005 | Berlin |
| 2006/0020007 | A1 | 1/2006 | Berlin |
| 2006/0020043 | A1 | 1/2006 | Berlin |
| 2006/0148735 | A1 | 7/2006 | Rosenzweig et al. |
| 2007/0065497 | A1 | 3/2007 | Guilford |
| 2007/0281045 | A1 | 12/2007 | Tripp et al. |
| 2008/0107638 | A1 | 5/2008 | Treadwell |
| 2008/0206155 | A1 | 8/2008 | Tamarkin et al. |
| 2008/0207748 | A1 | 8/2008 | Perez |
| 2008/0227747 | A1 | 9/2008 | Tabbiner |
| 2010/0143962 | A1 | 6/2010 | Cooper et al. |

FOREIGN PATENT DOCUMENTS

| WO | WO 9636316 A1 | 11/1996 |
| WO | WO 0051572 A1 | 9/2000 |
| WO | WO 03013474 A1 | 2/2003 |
| WO | WO 2006039268 A2 | 4/2006 |
| WO | WO 2007092509 A2 | 8/2007 |
| WO | WO 2009120919 A2 | 10/2009 |
| WO | WO 2011043237 A1 | 4/2011 |

OTHER PUBLICATIONS

Hans, Meredith, Nanoparticles for Drug Delivery, Section 23.3.1, 2006, Department of Materials Science and Engineering, Drexel University, Philadelphia, Pennsylvania, 8 pages.*
Adler, et al., "Association of systolic blood pressure with macrovascular and microvascular complications of type 2 diabetes (UKPDS 36): prospective observational study" BMJ, 321:412-419 (Aug. 12, 2000).
Aggarwal, "Signaling pathways to the TNF superfamily: a double-edged sword" Nat Rev Immunol. , 3(9):745-56 (Sep. 2003).
Aradhya, et al., "NF-kappaB signaling and human disease", Curr Opin Genet Dev., 11(3):300-6, (2001).
Bawa, "Nanoparticle-based therapeutics in Humans: a survey" Nanotechnology Law & Business, 5(2):135-155 (Summer 2008).
Dullens, et al., "Effects of emulsified policosanols with different chain-lengths on cholesterol metabolism in heterozygous LDL-receptor deficient mice" Journal of Lipid Research.
Dupont, "Overview of the lipid formulations of amphotericin B" Journal of Antimicrobial Chemotherapy, 49(Suppl. S1):31-36 (2002).
Garuda International, Inc., "LesstanoL® Policosanol 60 (Polycosanol) Raw Material" Accessed from: http://www.garudaint.com/prodspec.php?prod_code=OCTA-60, May 2007.
Garuda International, Inc., "LesstanoL® Octacosanol 95" Accessed from: http//www.garudaint.com.prodspec_pdf.php?prod_code=OCTA-95, Sep. 2004.
Ismael, et al., "Blockade of sensory abnormalities and kinin $B_1$ receptor expression by $N$-acetyl-$_L$-cysteine and ramipril in a rat model of insulin resistance" Eur J Pharmacol. 589:66-72 (2008).
Jain, "Hyperglycemia can cause membrane lipid peroxidation and osmotic fragility in human red blood cells", J. Biol Chem, 264(35):21340-21345 (1989).
Jain, et al., "Erythrocyte membrane lipid peroxidation and glycosylated hemoglobin in diabetes", Diabetes, 38(12):1539-43, (Dec. 1989).
Kassis, "Evaluation of cholesterol-lowering and antioxidant properties of sugar cane policosanols in hamsters and humans", School of Dietetics and Human Nutrition, McGill University, Montreal, Canada; 1-226 (Apr. 2008).
Kumar, et al., "Nuclear factor-kappaB: its role in health and disease", J Mol Med 82(7):434-48 (Jul. 2004).
Levy, et al., "Corrective homeostasis model assessment (HOMA) evaluation uses computer program", Diabetes Care, 21(12):2191-2 (Dec. 1998).
Marinangeli, et al., "Policosanols as nutraceuticals: fact or fiction" Critical Reviews of Food Science and Nutrition, 50:259-267 (2010).
Meng, et al., "Akt is a downstream target of NF-kappB", J. Biol. Chem, 277(33):29674-26980 (Aug. 16, 2002).
Michael, et al., "Loss of Insulin Signaling in Hepatocytes Leads to Severe Insulin Resistance and Progressive Hepatic Dysfunction" Molecular Cell, 6:87-97 (2000).

(Continued)

*Primary Examiner* — Alton Pryor
(74) *Attorney, Agent, or Firm* — Morgan, Lewis & Bockius LLP; Jeffrey S. Mann; Ada O. Wong

(57) ABSTRACT

The present invention provides nanoparticulate policosanol, formulations including these particles, as a well as methods of using the particles and formulations for treatment and prophylaxis of various diseases and conditions.

14 Claims, 29 Drawing Sheets

(56) References Cited

OTHER PUBLICATIONS

Nishikimi, et al., "Molecular basis for the deficiency in humans of gulonolactone oxidase, a key enzyme for ascorbic acid biosynthesis", Am J Clin Nutr, 54:1203S-1208S (1991).

Shea, et al., "Nanosphere-mediated delivery of vitamin E increases its efficacy against oxidative stress resulting from exposure to amyloid beta" Journal of Alzheimer's Disease, 7:1-5 (2005).

Stratton, et al. "Association of glycaemia with macrovascular and microvascular complications of type 2 diabetes (UKPDS 35): prospective observational study" BMJ, 321: 412-419 (Aug. 12, 2000).

Yamamoto, et al., "Role of the NF-kappaB pathway in the pathogenesis of human disease states", Curr Mol Med. 1(3):287-96 (Jul. 2001).

Yan, et al., "Efficacy of hypochlorlous acid scavengers in the prevention of protein carbonyl formation" Arch Biochem Biophys 327(2):330-334 (Mar. 15, 1996).

Yaturu, et al., "Resistin and adiponectin levels in subjects with coronary artery disease and type 2 diabetes", Cytokine, 34(3-4): 219-23 (May 2006).

Yerneni, et al., "Hyperglycemia-induced activation of nuclear transcription factor kappaB vascular smooth muscle cells", Diabetes, 48:855-64 (1999).

\* cited by examiner

POLICOSANOL NANOPARTICLES

CROSS-REFERENCE TO RELATED APPLICATION

This application claims the benefit of priority to U.S. Provisional Patent Application No. 61/154,712, filed on Feb. 23, 2009, which is hereby incorporated by reference in its entirety.

FIELD OF THE INVENTION

The present invention relates to nanoparticulate compositions comprising at least one policosanol, novel nanoparticulate policosanol formulations, and uses thereof. In various embodiments, the nanoparticulate policosanol particles have an effective average particle size of less than about 100 nm. The nanoparticulate policosanol particles can have a size of between about 40 nm and about 100 nm.

BACKGROUND OF THE INVENTION

Policosanol is a complex mixture of concentrated long chain N-alkyl alcohols derived from plant sources, such as sugar cane. Early work in Cuba studying the effects of policosanol on serum lipid and lipoprotein levels in healthy volunteers indicated that, at dosages of 2-40 mg/d, policosanol administration reduced serum lipid and lipoprotein levels (Hernandez et al., *Curr. Ther. Res. Clin. Exp.* 1992; 51: 568), and reduced hypercholesterolemia (Pons et al., *Curr. Ther. Res. Clin. Exp.;* 1992; 52: 507). However, despite numerous subsequent studies, researchers outside Cuba have been unable to verify the claims made in conjunction with the original research. The ineffectiveness of policosanol on serum lipid/cholesterol levels has been comprehensively documented in respected, peer-reviewed journals.

For example, Francini-Pesenti and coworkers conducted double blinded, randomized, placebo-controlled trials of policosanol in subjects with hypercholesterolemia and concluded that doses of 10 mg/d and 20 mg/d of policosanol showed no lipid lowering effects (*Complement Ther. Med.;* 2008; 16(2): 61; and *Phytother. Res.;* 2008; 22(3): 318). In a similar blind, placebo-controlled study, Berthold and coworkers showed that doses of 10, 20, 40 and 80 mg/d of policosanol did not result in lower serum lipid levels than those seen in subjects to whom the placebo was administered (*JAMA;* 2006; 295(19): 2262). Dullens et al. found that neither individual policosanol components (C24, C26, C28, or C30) nor the natural policosanol mixture (all components, 30 mg/100 g diet) lowered serum cholesterol concentrations in LDL receptor knockout mice (*J. Lipid Res.;* 2008; 49(4): 790). Kassis and coworkers studied the efficacy of Cuban sugar cane policosanols for treating hypercholesterolemia in humans at a dosage of 10 mg/d and concluded that policosanol had no beneficial effects on lipid indicators in hypercholesterolemic subjects (*Am. J. Clin. Nutr.;* 2006; 84(5): 1003). Lin and coworkers studied the effects of 20 mg/d dosages of wheat germ policosanol in subjects with normal to mildly elevated plasma cholesterol and detected no lowering of plasma cholesterol (*Metabolism;* 2004; 53(10): 1309). Lukashevich et al. found that beeswax policosanol (10 mg or 40 mg) administered daily in tablet or soft gel formulations had no effect on serum lipids in subjects with mild-to-moderate hypercholesterolemia. (*Circulation;* 2006; 114: 892). Murphy et al. found dietary supplementation of rabbits with policosanol from sunflower oil did not have any cholesterol lowering effect. (*J. Am. College Nutr;* 2008; 27(4): 476).

Thus, despite the early apparently promising results of the Cuban research, the conclusion that must be reached from contemporary blinded, placebo-controlled studies is that art-recognized policosanol formulations are not effective at modulating serum lipid/cholesterol levels.

Research on the utility of policosanol formulations on other metabolic and physiologic parameters has produced similarly negative results. For example, policosanol was shown to have no effect on blood sugar levels, glycemic control (Crespo et al., *Int. J. Clin. Pharm. Res.;* 1999: 117) or diabetic status (Shinbori et al., *Eur. J. Pharmacol;* 2007; 139-144).

A controversy existed for a time regarding whether the composition or formulation of the policosanol used in the Cuban studies was responsible for the inconsistent results between the Cuban research and that of other workers. This controversy has been put to rest in seminal research. (Kassis, *British Journal of Nutrition* (2007), 97, 381-388; Kassis, *Lipids Health Dis.*(2008); 7:17; Kassis *Appl. Physiol. Nutr. Metab*; (2008); 33(3): 540 and Dullens *J. Lipid Res.* (2008), 49: 790). They studied utilized different sugar cane derived policosanol formulations, including the formulation used in the Cuban research. Their studies concluded that none of the tested policosanol formulations significantly improved lipid parameters in humans or animals relative to the control. Moreover, the in vivo assessment of LDL oxidation showed no significant alteration in oxidized LDL concentration relative to the baseline and control. Thus, as of mid-2008, the controversy regarding the serum lipid lowering effects of the Cuban as well as other sugar cane policosanol formulations is resolved outside Cuba

SUMMARY OF THE INVENTION

The present invention provides nanoparticles and nanoparticulate formulations of policosanol as well as methods for making these nanoparticles and formulations. Quite surprisingly, the policosanol formulations of the invention lower cholesterol and serum lipids. and reduce systolic and diastolic blood pressure. Moreover, the formulations of the invention exert antioxidant effects, mitigate insulin resistance and its consequences, raise vitamin C levels and regulate blood sugar levels. Accordingly, the invention also provides methods of treating disease and regulating metabolism by administering to a subject a formulation of the invention. The invention also provides methods of regulating metabolism and treating hypertension, hypercholesterolemia as well as several other diseases. For example, the formulation of the invention is of use in controlling in vivo protein oxidation, regulating blood glucose levels, and can be used to treat and prevent insulin resistance and its consequences, e.g., diabetes, and the deleterious downstream effects thereof. Moreover, the formulations of the invention are of use in regulating in vivo vitamin C levels in a subject.

Thus, in various embodiments, the invention provides a nanoparticle of policosanol. A representative nanoparticle of the invention includes a policosanol fraction comprising about 60% to about 95%, e.g., from about 70% to about 95% octacosanol; and a stabilizer fraction. In an exemplary embodiment, the stabilizer fraction includes a poly (ethylene glycol) ester. In various embodiments, the stabilizer fraction includes a tocopheryl ester. Exemplary components of the stabilizer fraction include tocopheryl poly (ethylene glycol) esters, e.g., tocopheryl polyethylene glycol (1000) succinate ("TPGS"). Exemplary nanoparticles of the invention have a diameter of less than about 100 nm.

Other objects, advantages, and embodiments of the invention are set forth in the detailed description that follows.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended Figures. These Figures form a part of the specification. It is to be noted, however, that the appended Figures illustrate preferred embodiments of the invention and therefore are not to be considered limiting in their scope.

DETAILED DESCRIPTION OF THE INVENTION AND THE PREFERRED EMBODIMENTS

Definitions

Figure 1:
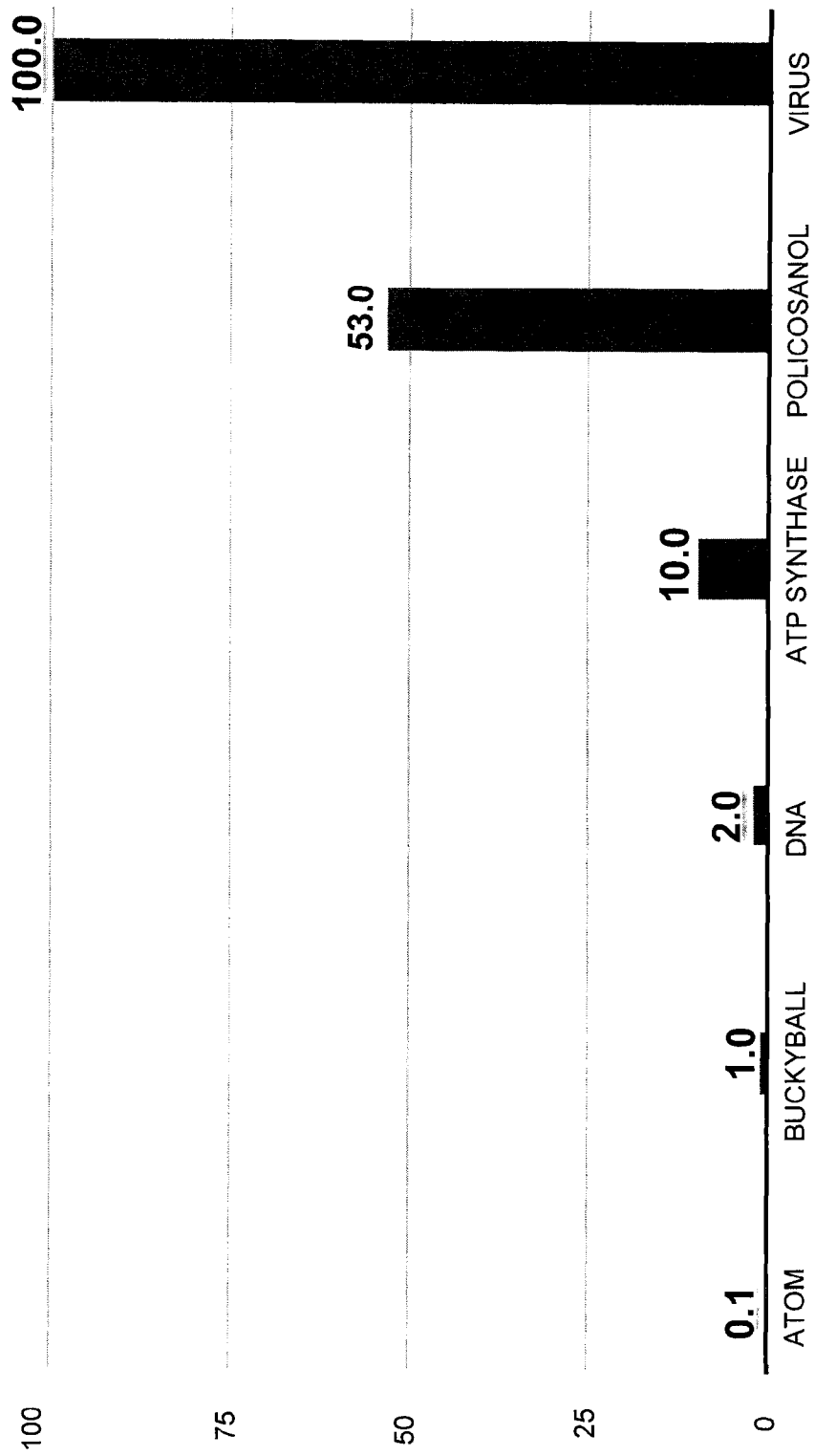
FIG. 1 shows the size of the size of the particles of the invention relative to other nanoparticles.
Figure 2:
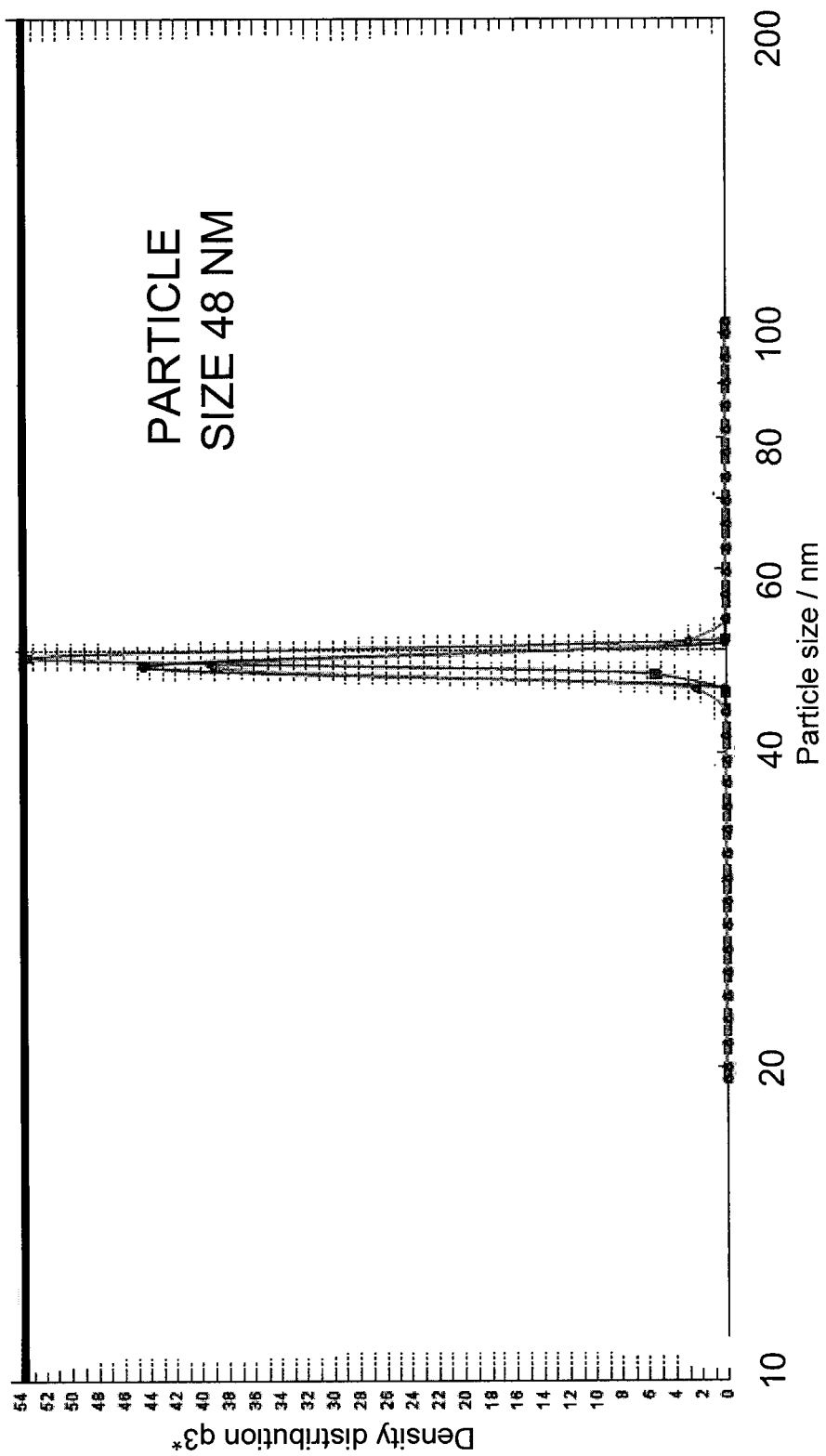
FIG. 2 shows the size distribution of nanoparticles of the invention with a peak at about 48 nm as measured by light scattering.
Figure 3:
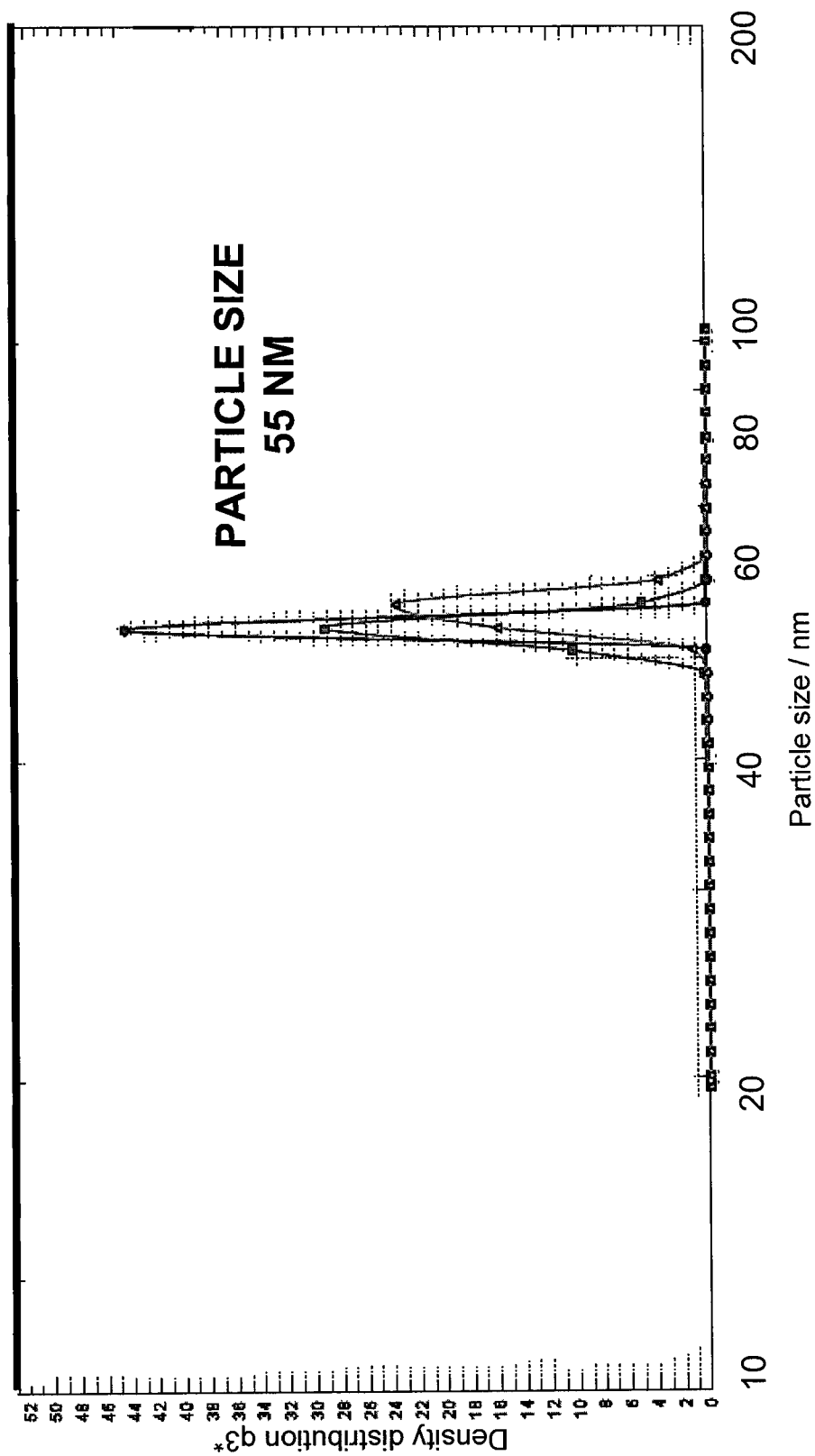
FIG. 3 shows the size distribution of nanoparticles of the invention with a peak at about 55 nm as measured by light scattering.
Figure 4:
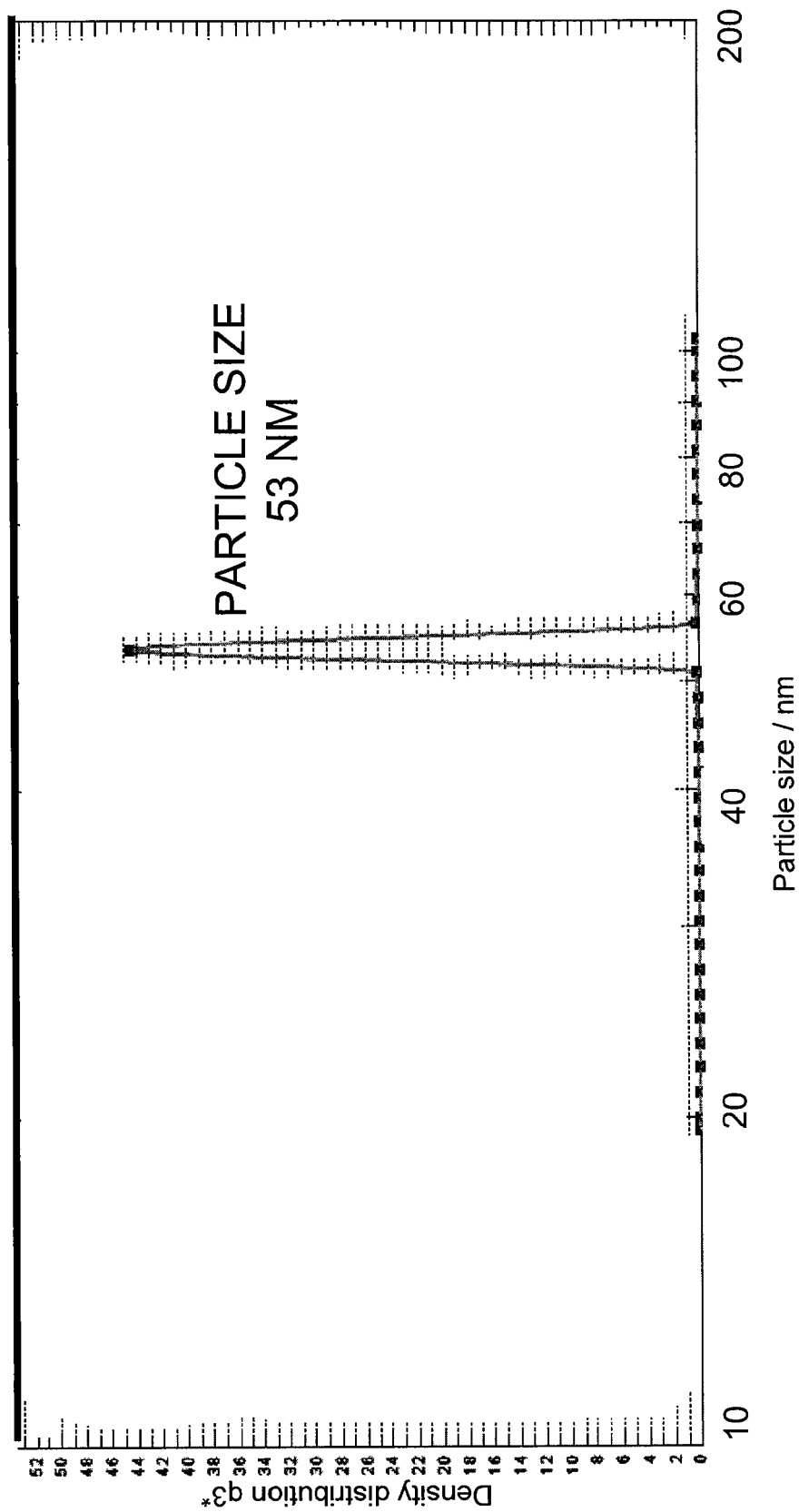
FIG. 4 shows the size distribution of nanoparticles of the invention with a peak at about 53 nm as measured by light scattering.
Figure 5:
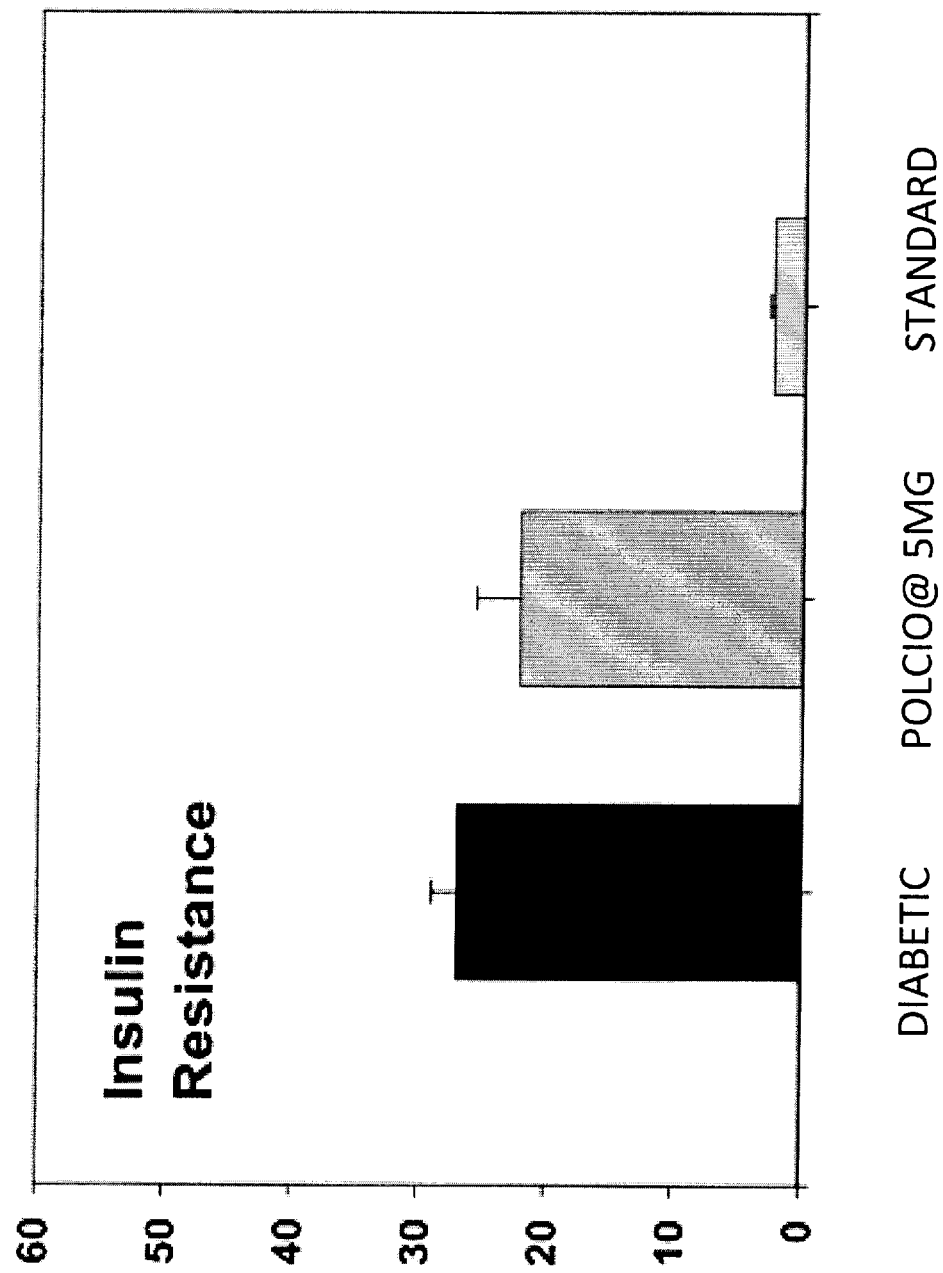
FIG. 5 shows levels of insulin resistance in untreated rats and rats treated with particles of the invention at 1 mg/kg and 2 mg/kg.
Figure 6:
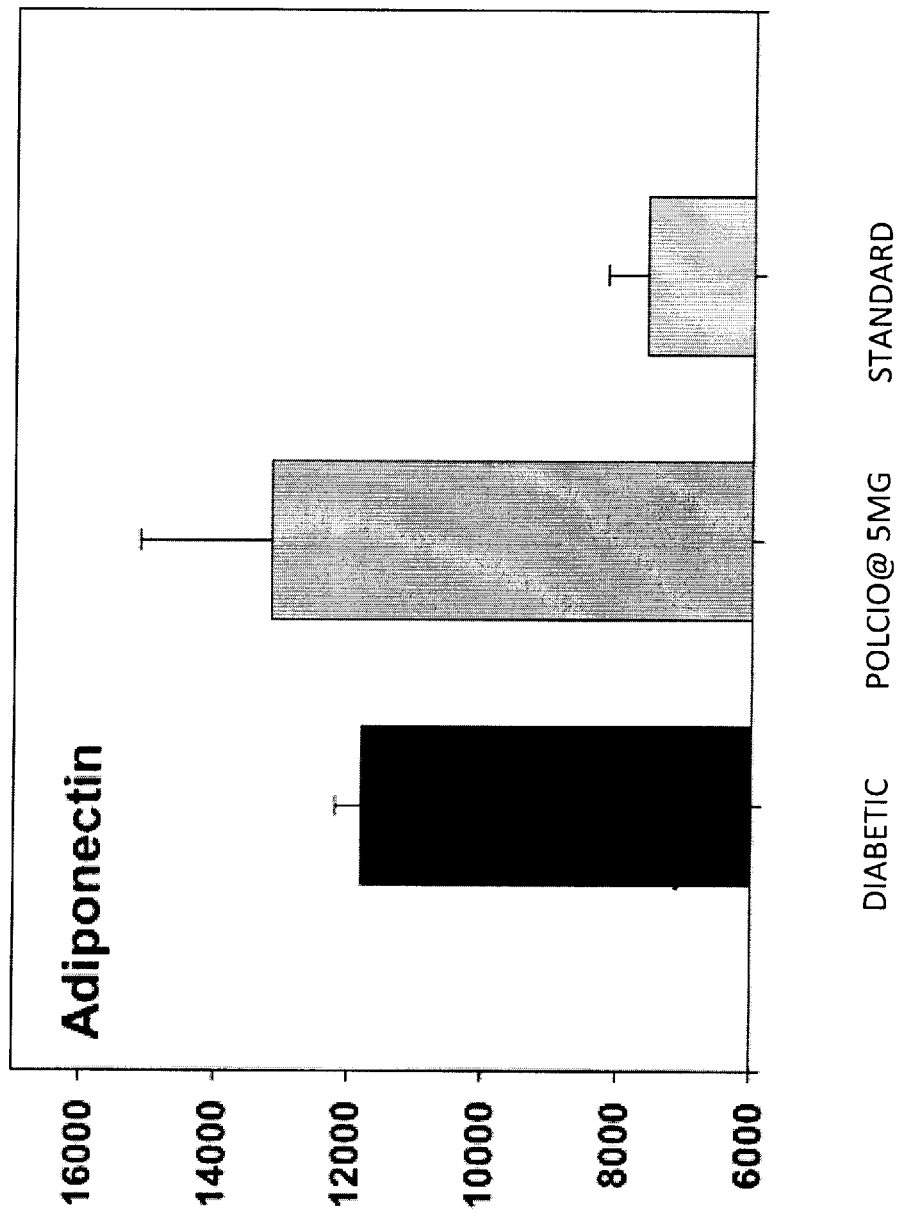
FIG. 6 shows plasma levels of adiponectin in untreated rats and rats treated with particles of the invention.
Figure 7:
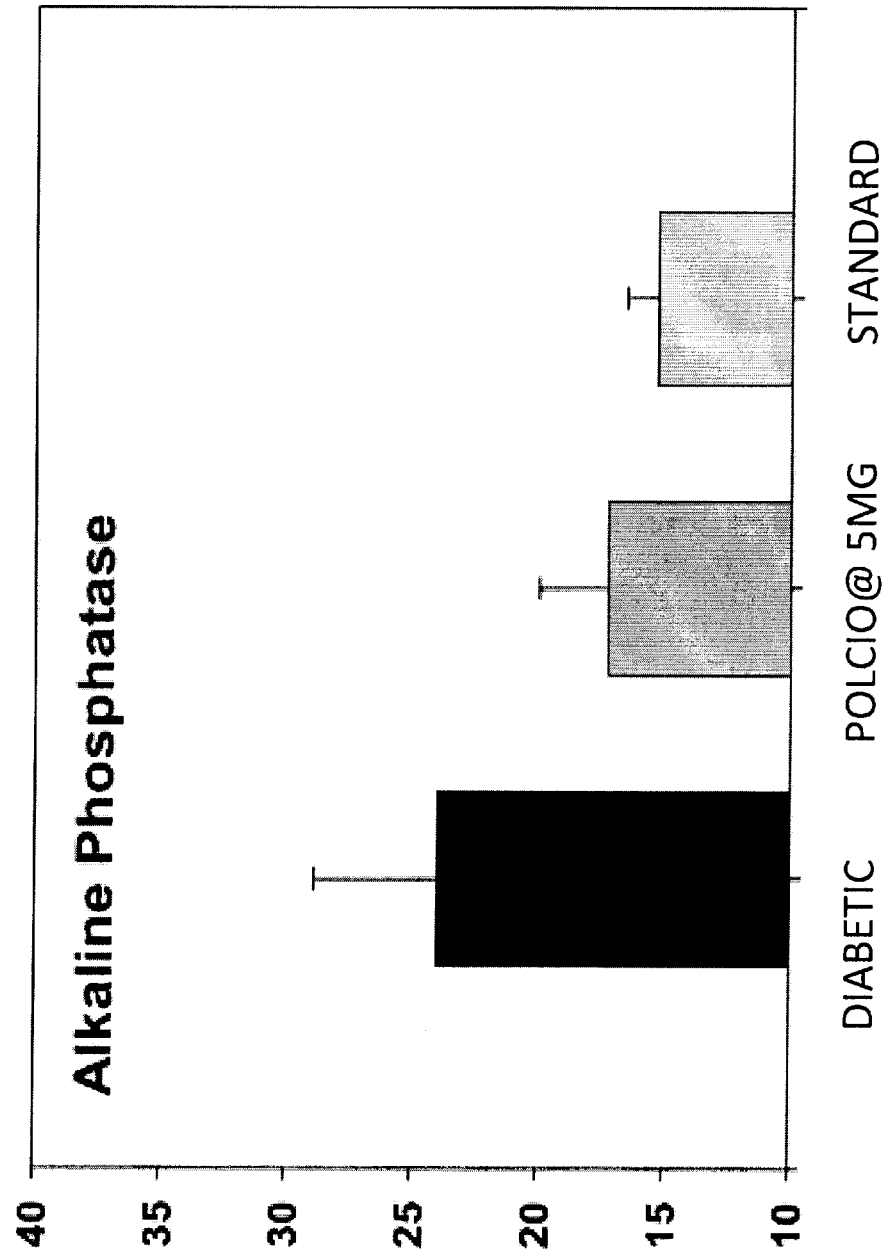
FIG. 7 shows blood levels of alkaline phosphatase in untreated rats and rats treated with particles of the invention at 1 mg/kg and 2 mg/kg.
Figure 8:
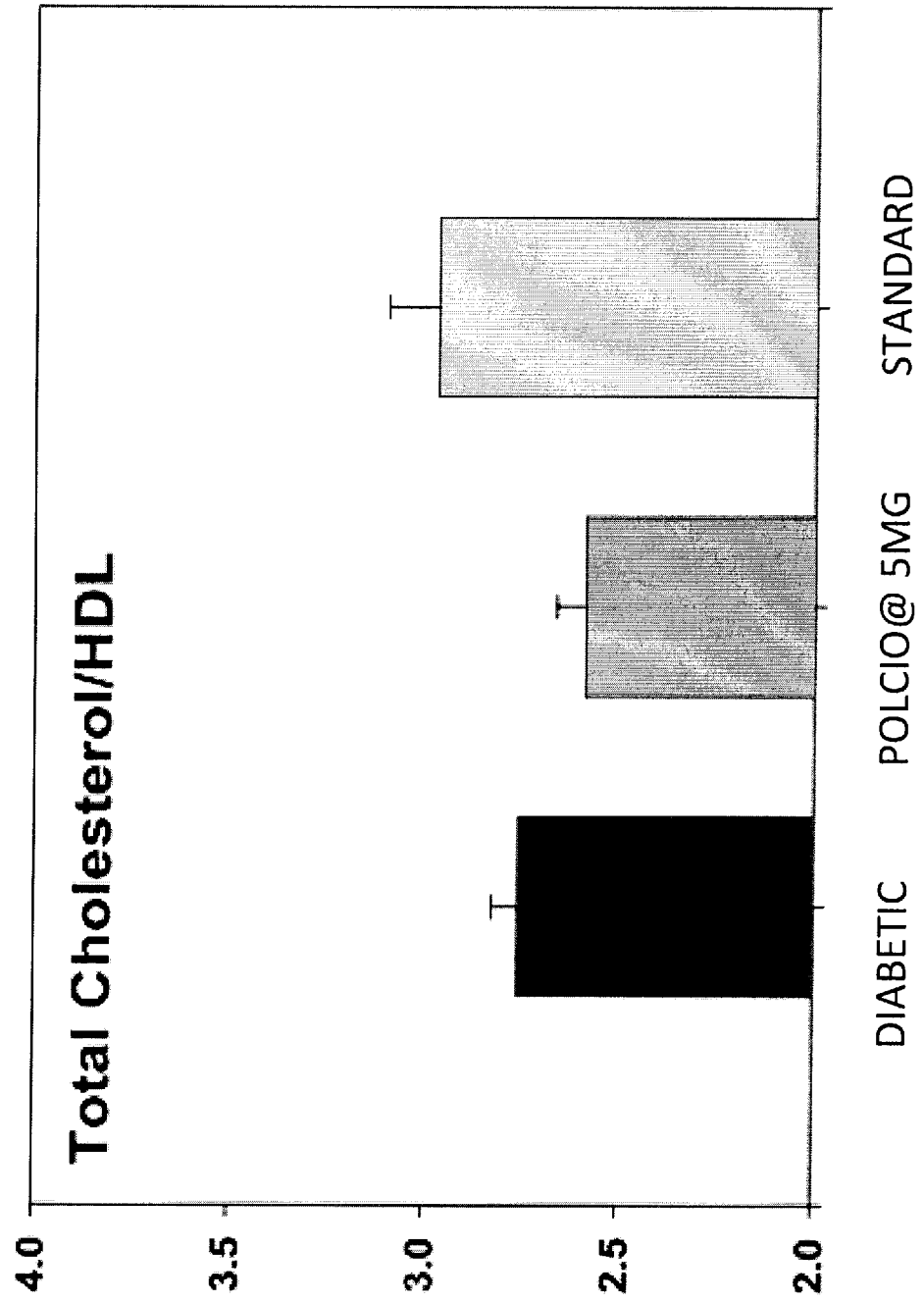
FIG. 8 shows levels of total cholesterol/HDL ratio in untreated rats and rats treated with particles of the invention at 1 mg/kg and 2 mg/kg.
Figure 9:
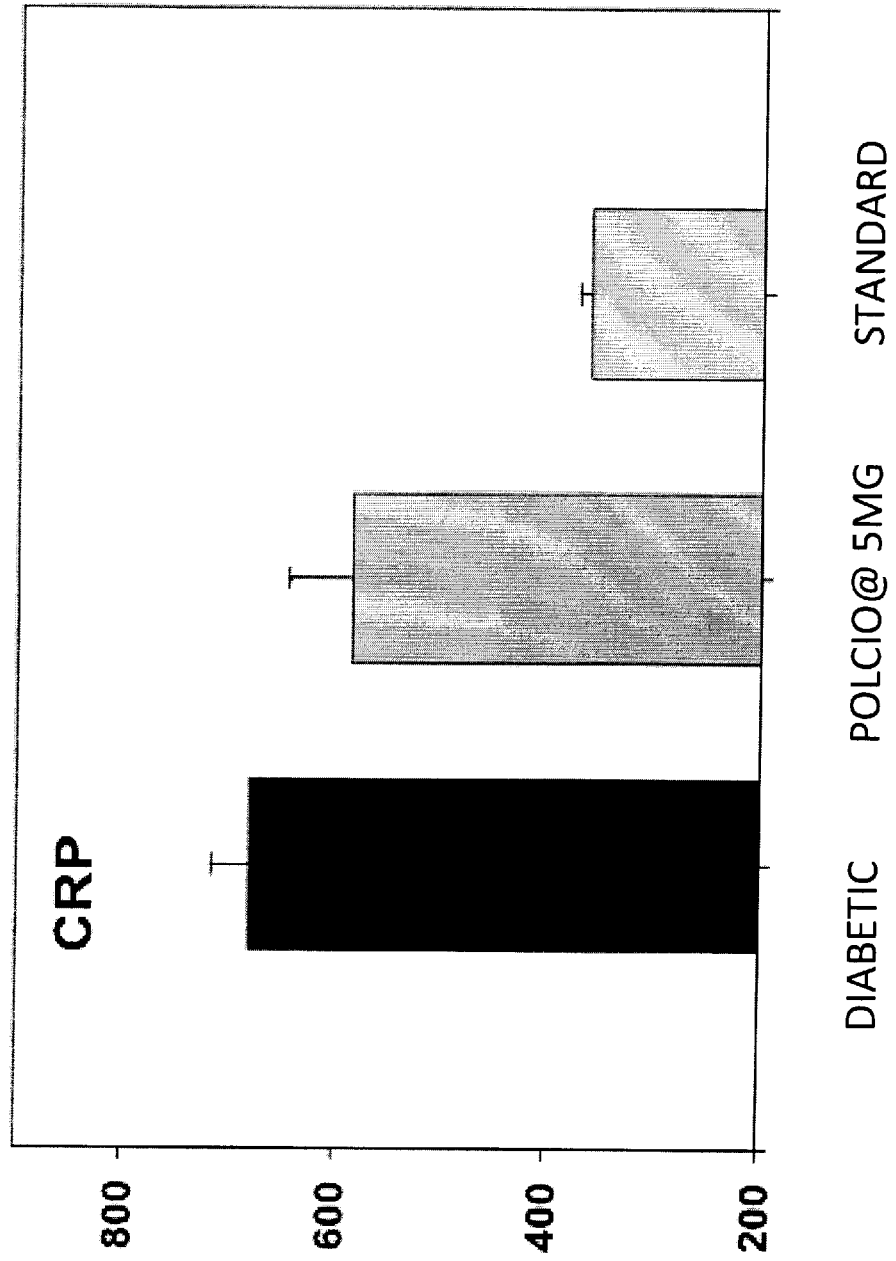
FIG. 9 shows blood levels of C-reactive protein in untreated rats and rats treated with particles of the invention at 1 mg/kg and 2 mg/kg.
Figure 10:
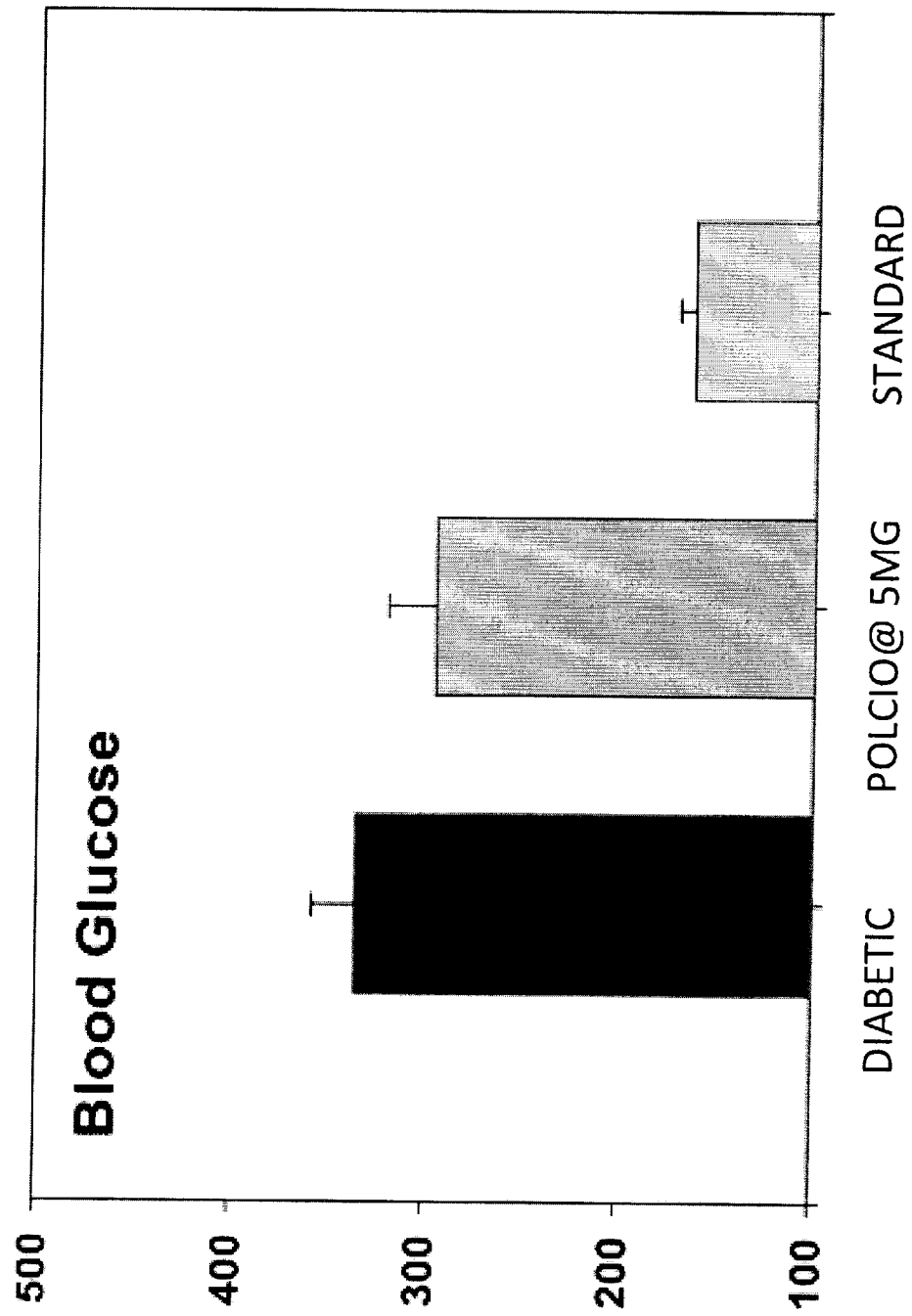
FIG. 10 shows fasting blood glucose levels in untreated rats and rats treated with particles of the invention.
Figure 11:
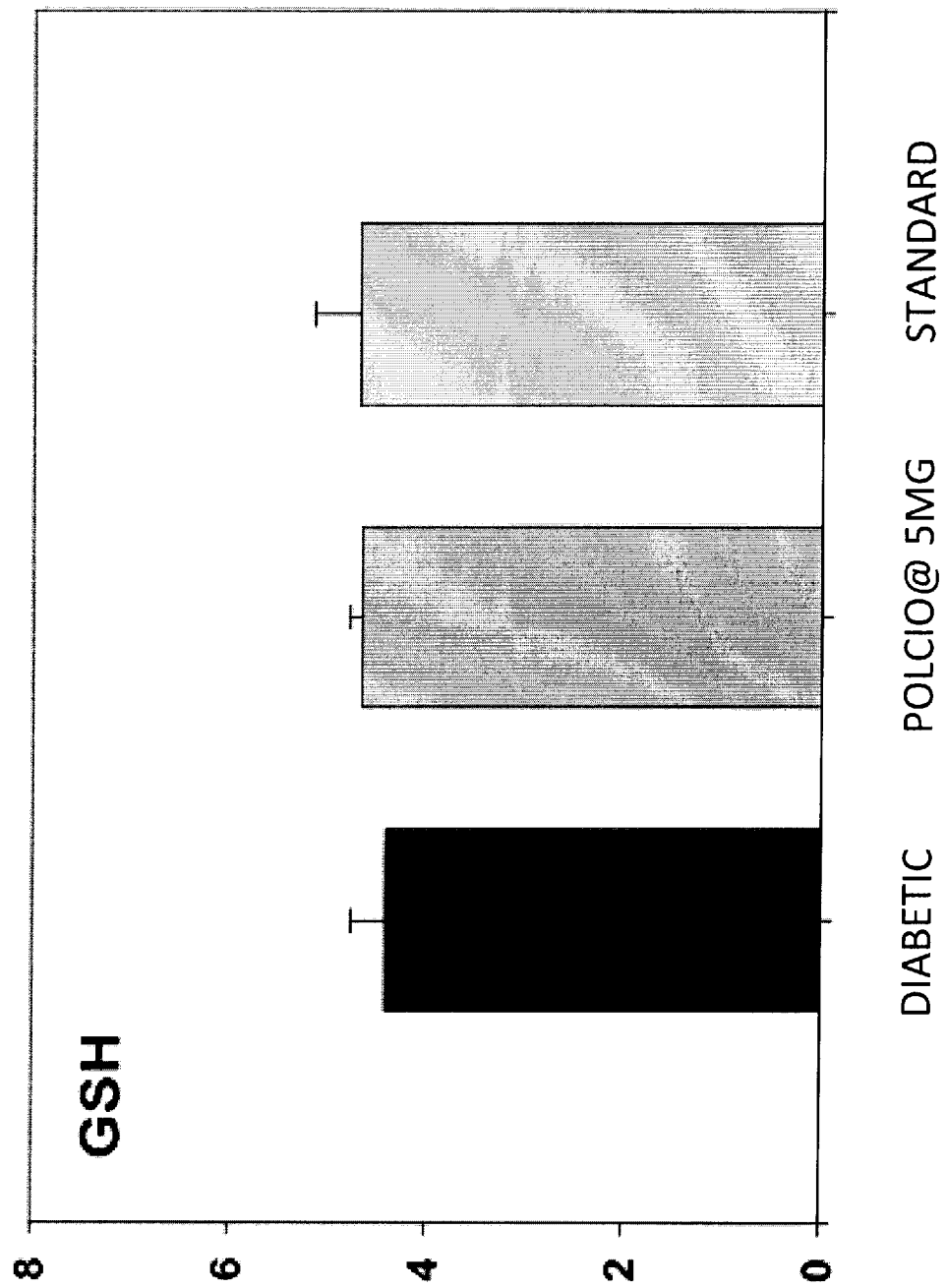
FIG. 11 shows glutathione levels in untreated rats and rats treated with particles of the invention.
Figure 12:
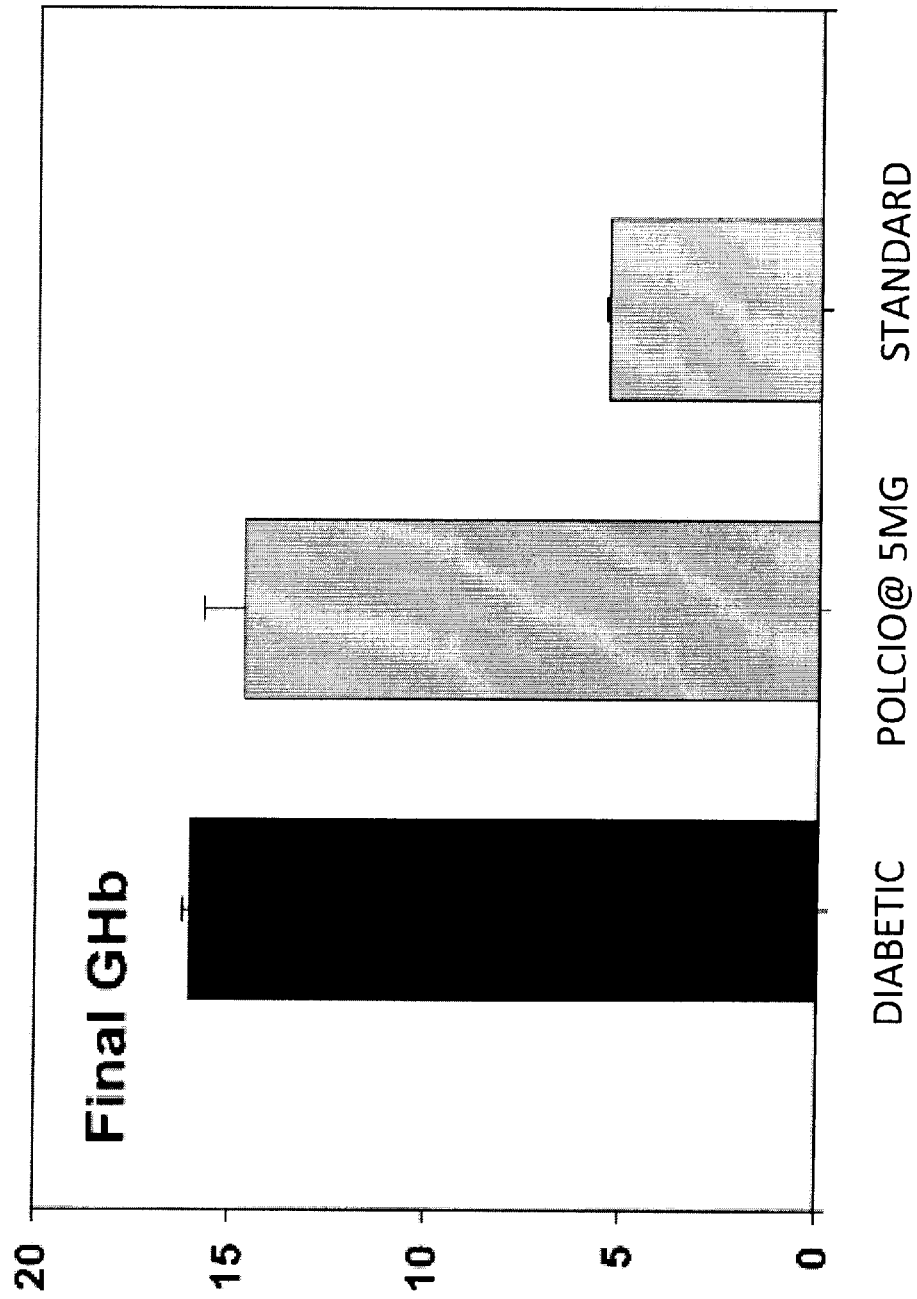
FIG. 12 shows levels of glycosylated hemoglobin (HbA1c) levels in untreated rats and rats treated with particles of the invention.
Figure 13:
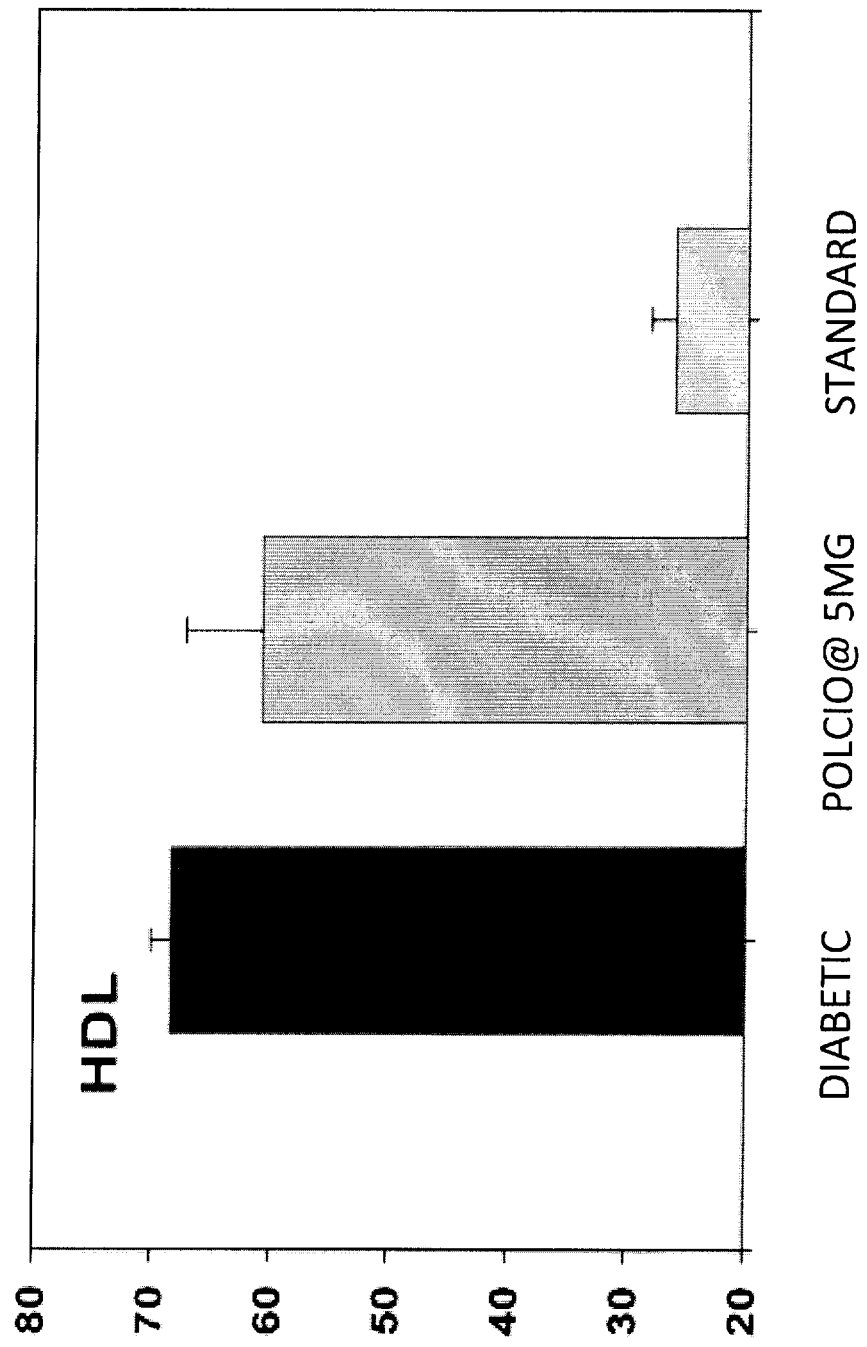
FIG. 13 shows HDL levels in untreated rats and rats treated with particles of the invention.
Figure 14:
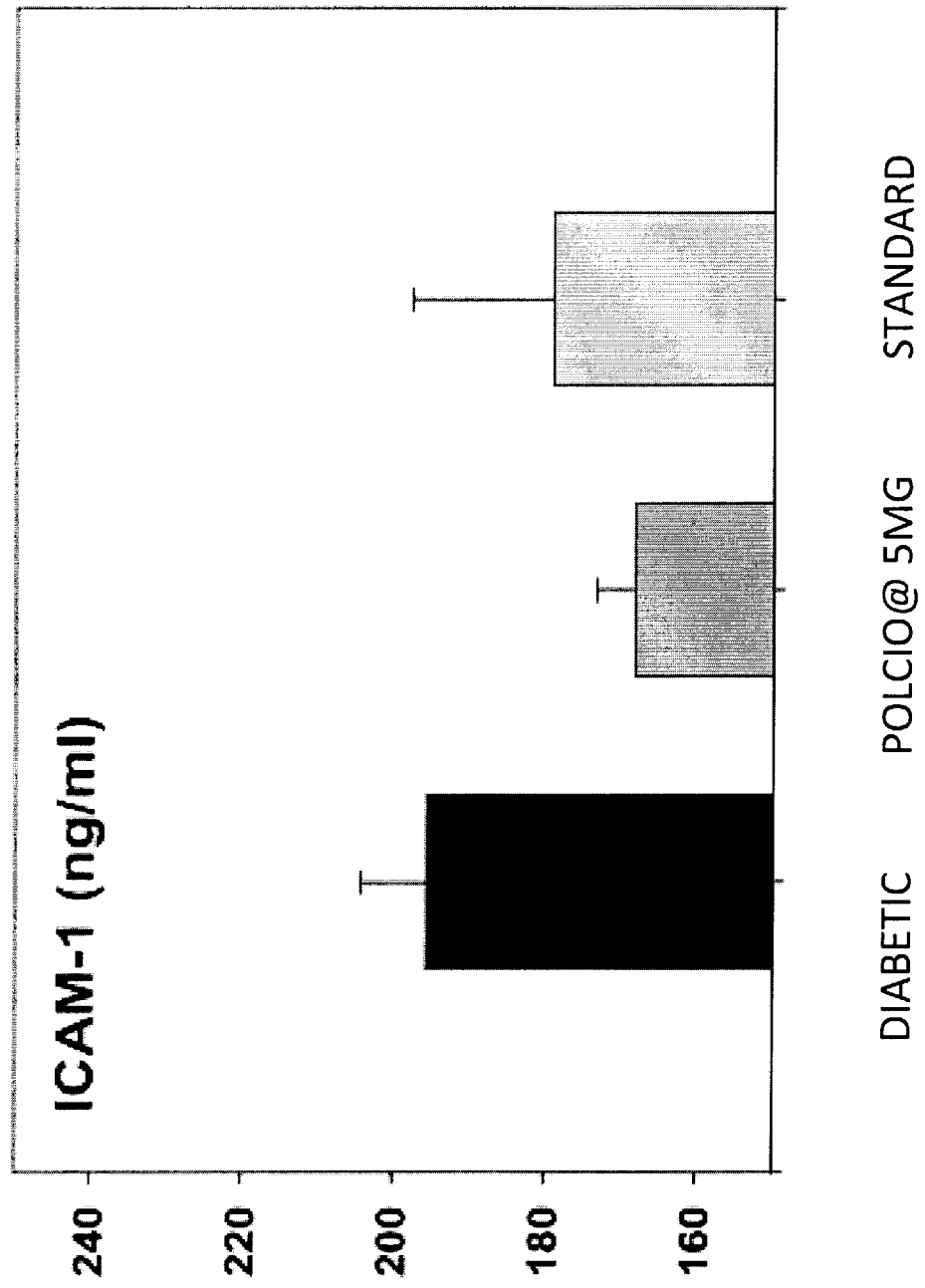
FIG. 14 shows the ICAM-1 (inter cellular adhesion molecule) levels in untreated rats and rats treated with particles of the invention.
Figure 15:
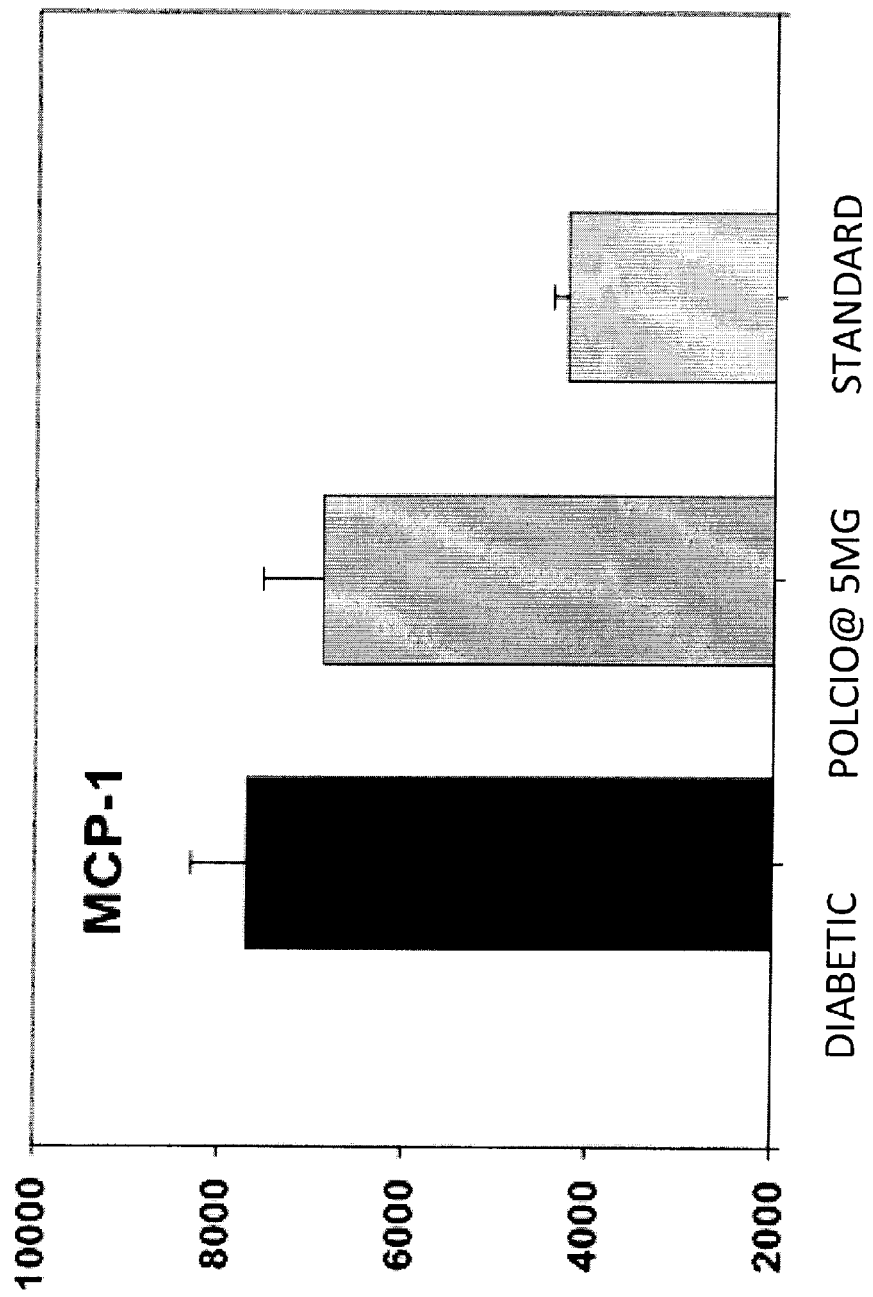
FIG. 15 shows MCP-1 (monocyte chemotactic protein-1) levels in untreated rats and rats treated with particles of the invention.
Figure 16:
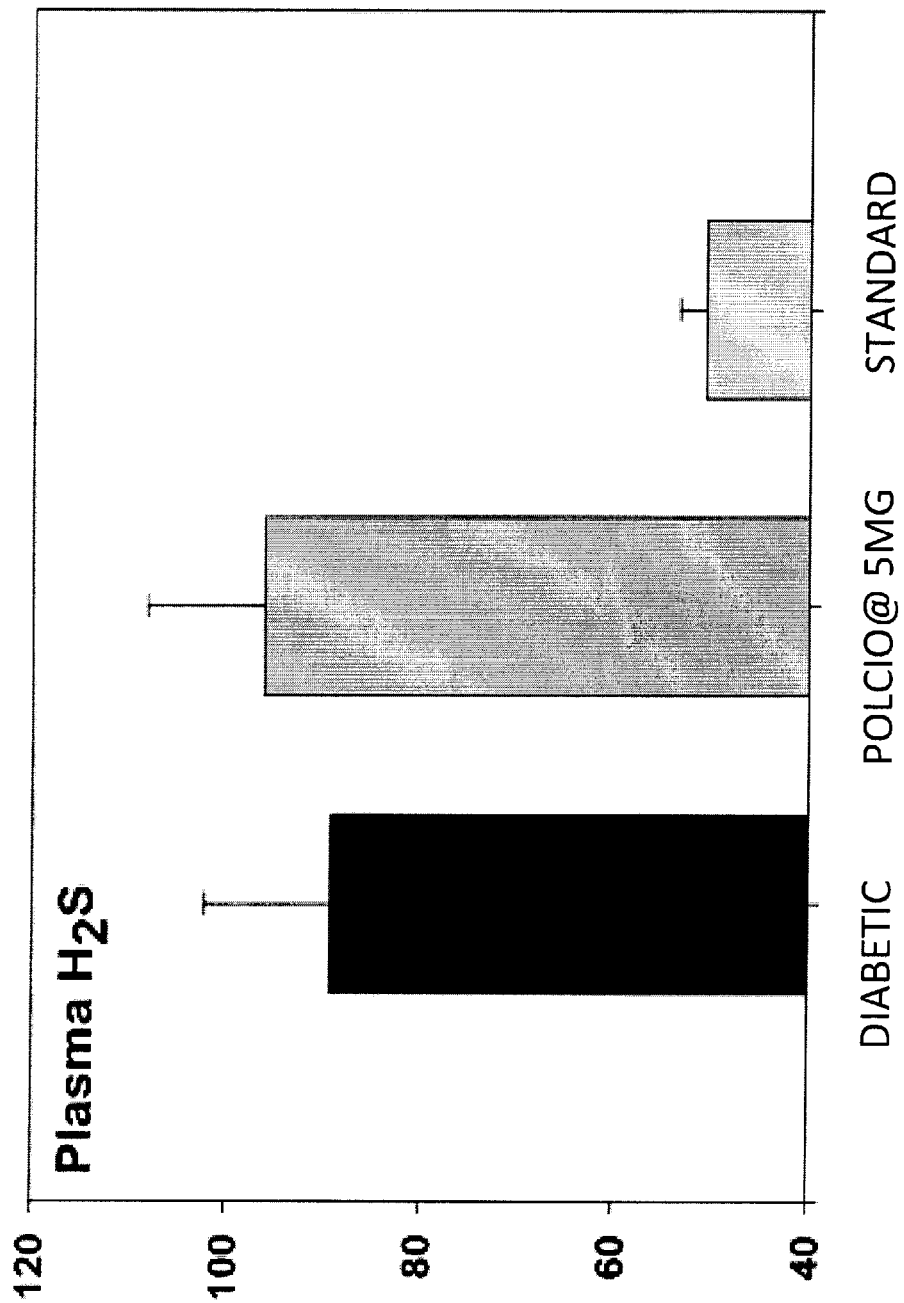
FIG. 16 shows levels of plasma $H_2S$ (hydrogen sulfide) in untreated rats and rats treated with particles of the invention.
Figure 17:
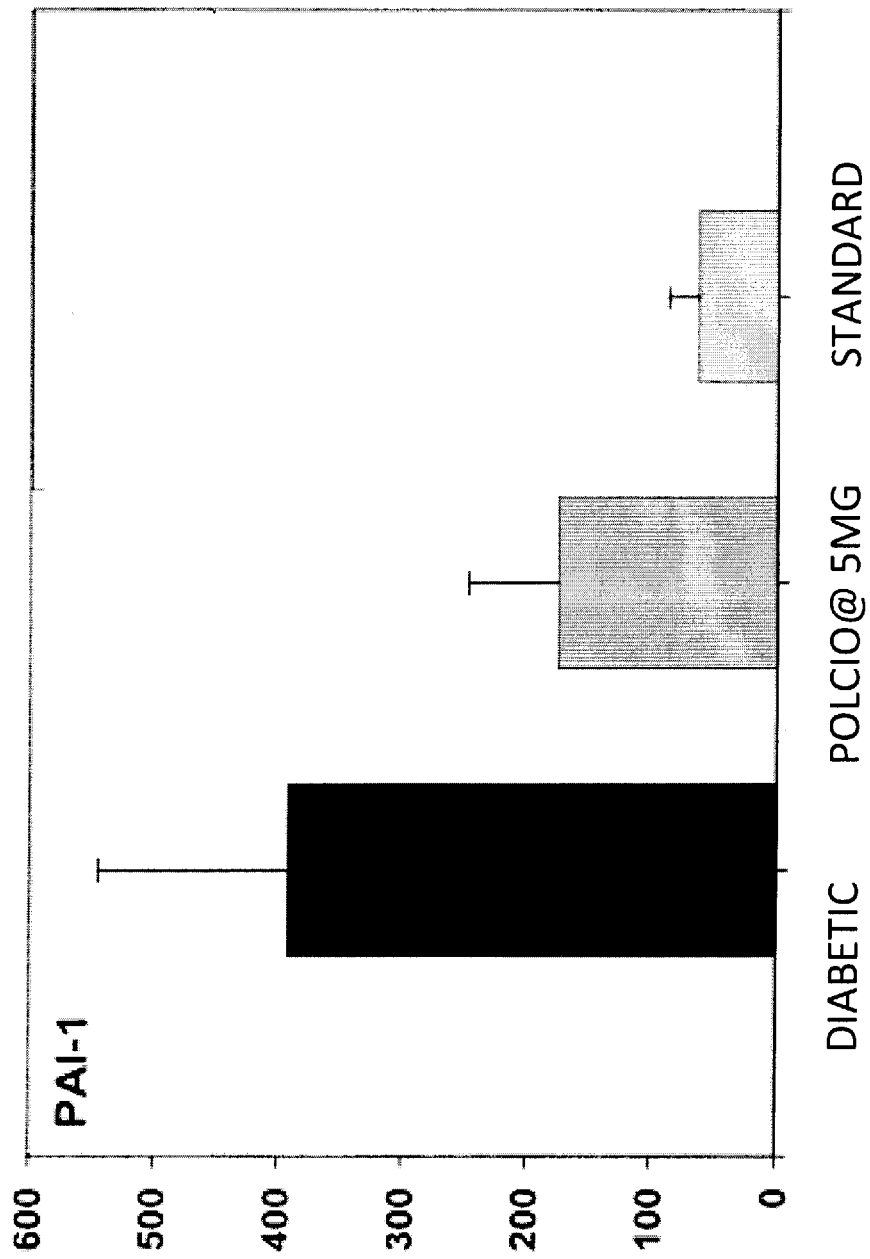
FIG. 17 shows PAI-1 (plasminogen activation inhibitor) levels in untreated rats and rats treated with particles of the invention.
Figure 18:
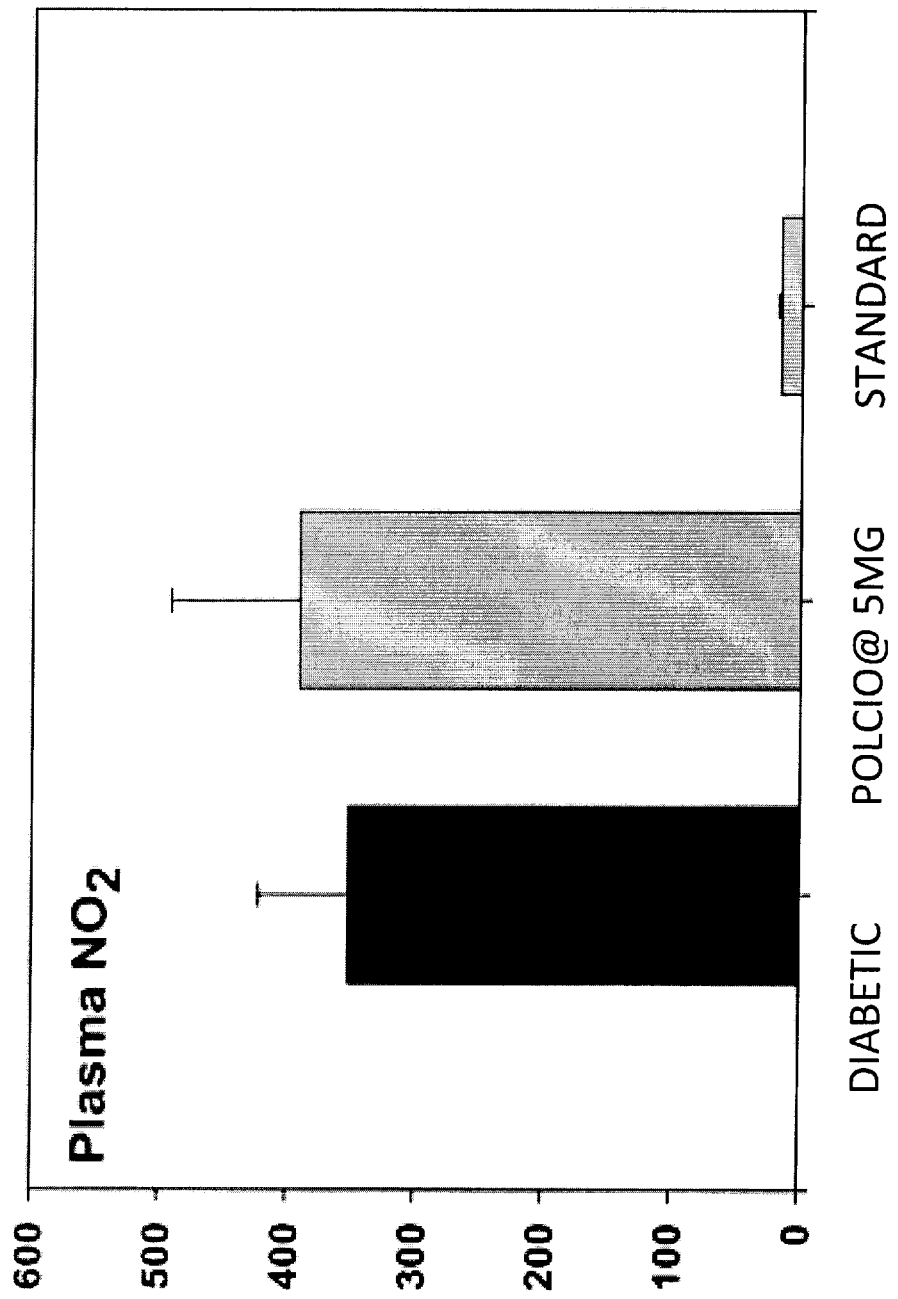
FIG. 18 shows nitric oxide levels in untreated rats and rats treated with particles of the invention.
Figure 19:
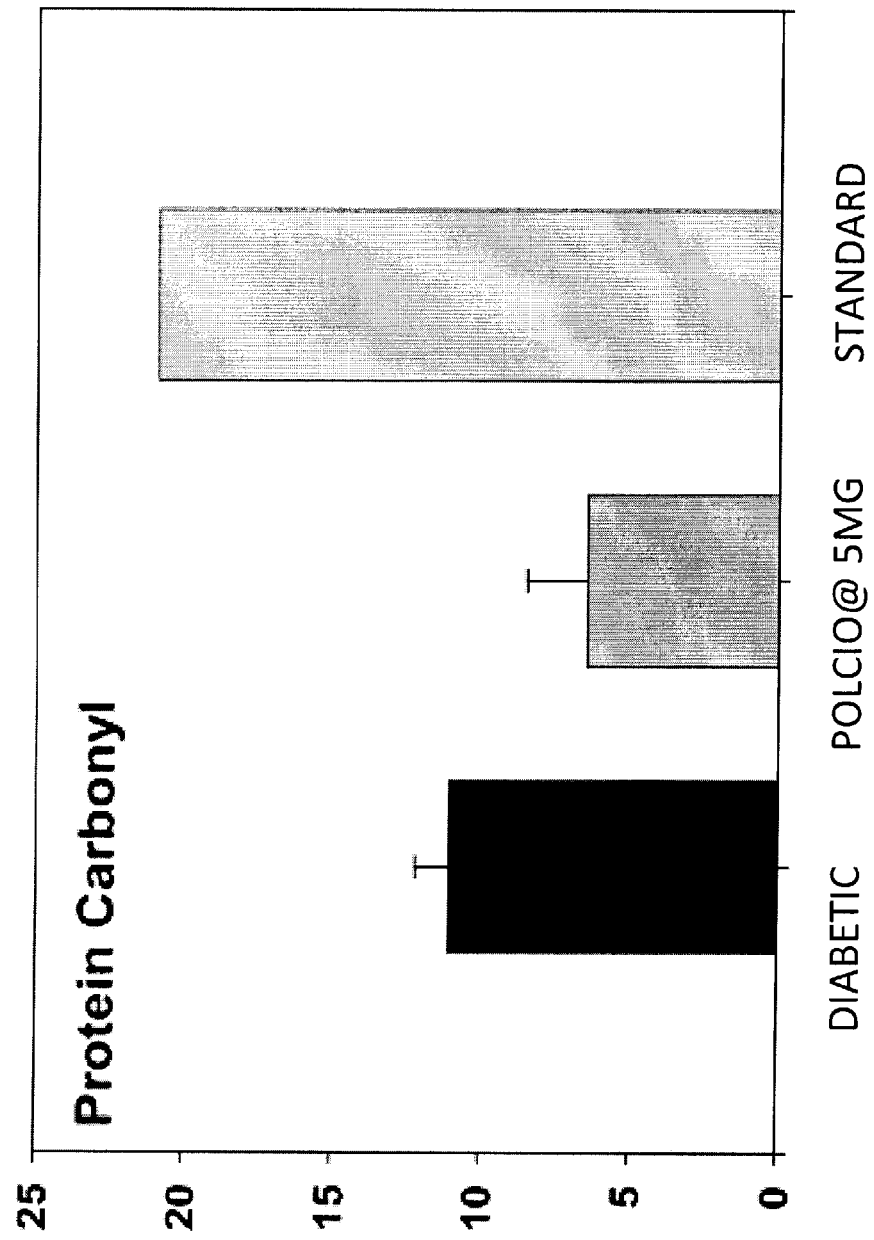
FIG. 19 shows protein oxidation levels in untreated rats and rats treated with particles of the invention.
Figure 20:
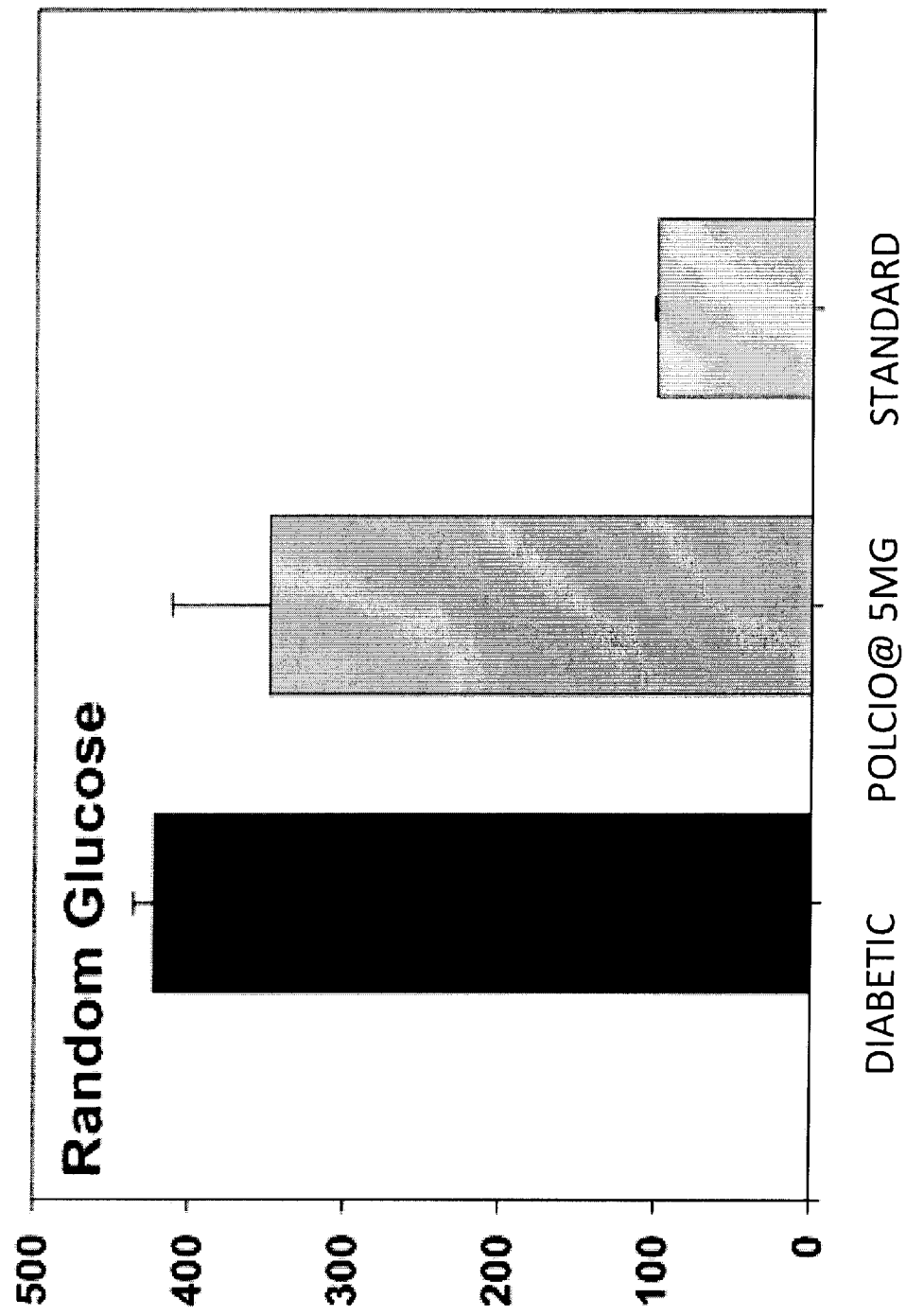
FIG. 20 random glucose levels in untreated rats and rats treated with particles of the invention.
Figure 21:
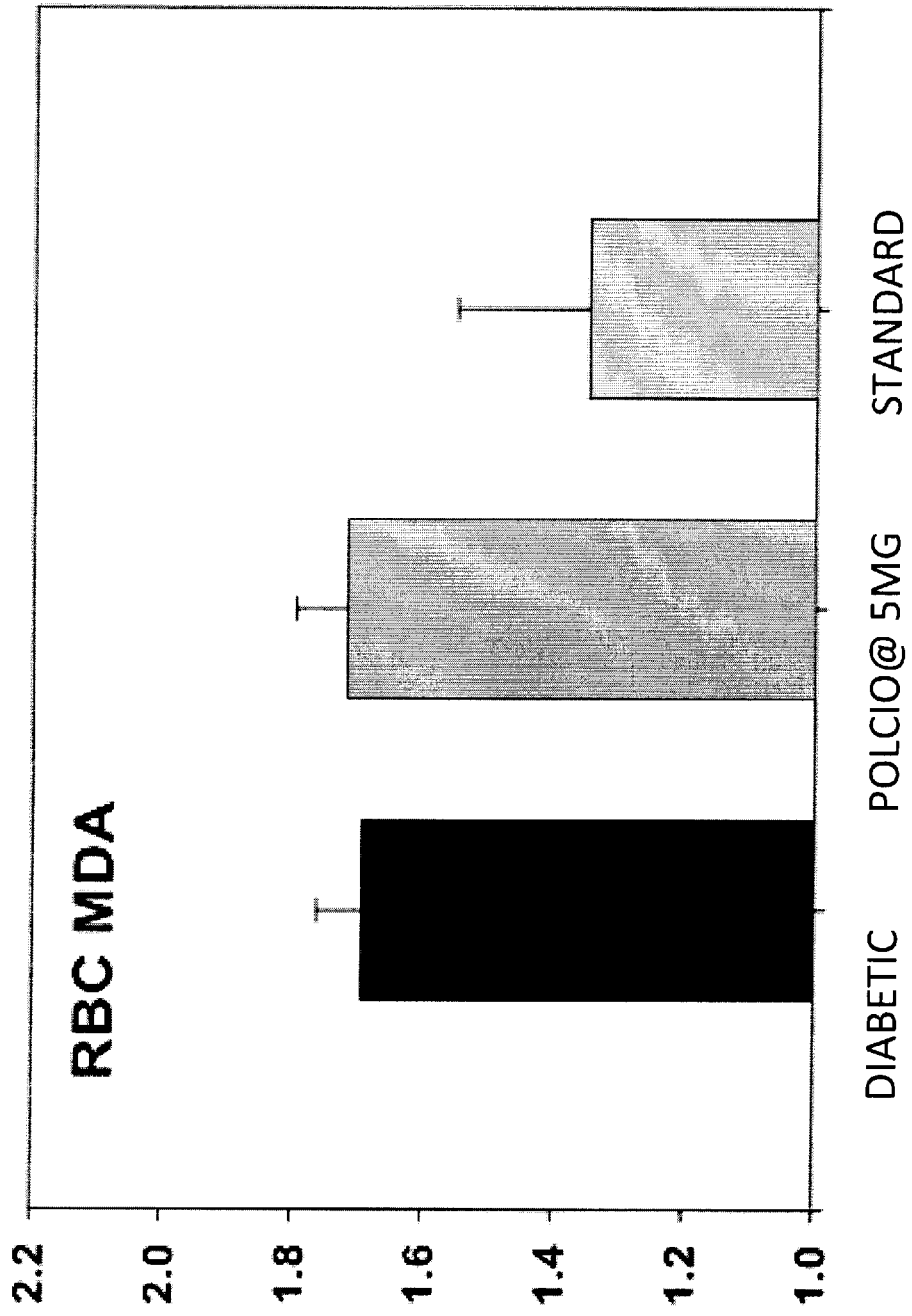
FIG. 21 shows red blood lipid peroxidation levels in untreated rats and rats treated with particles of the invention.
Figure 22:
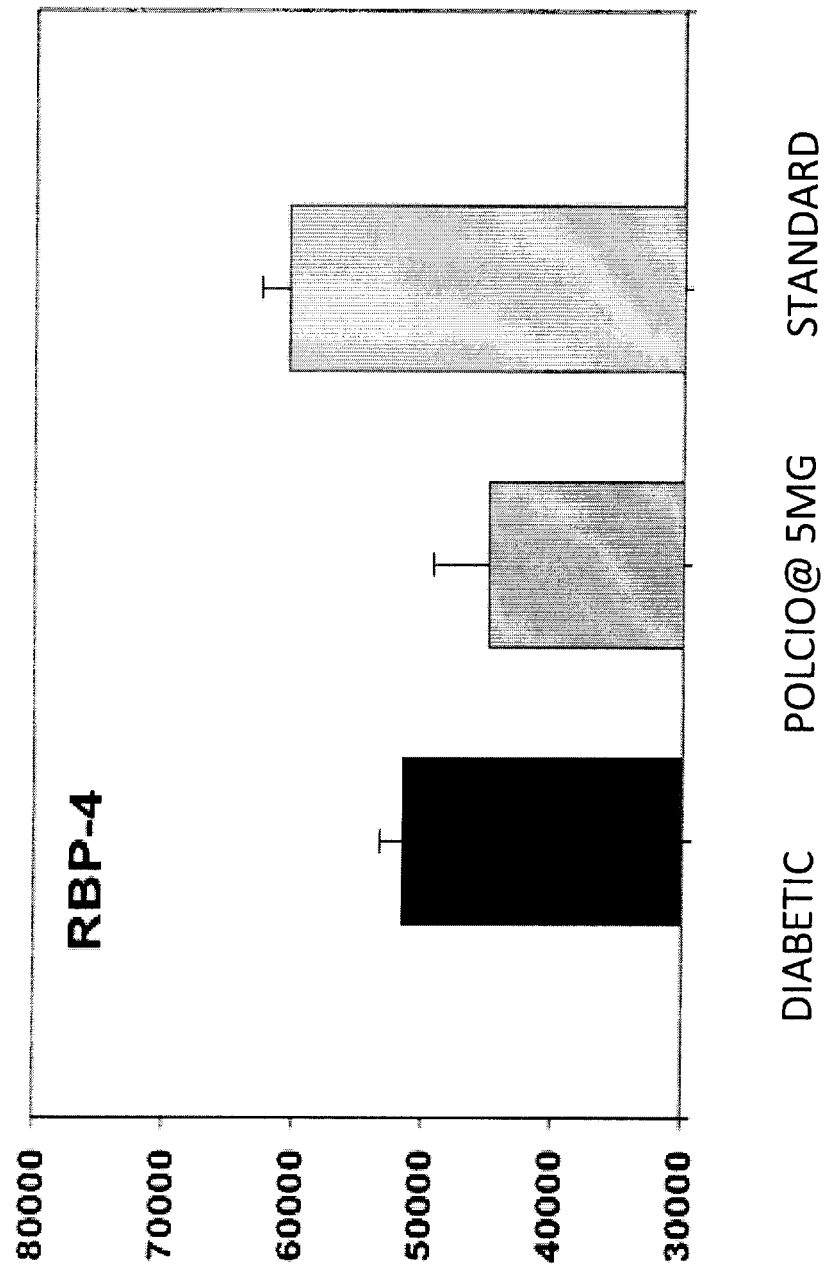
FIG. 22 shows RBP-4 (retinal binding protein) levels in untreated rats and rats treated with particles of the invention.
Figure 23:
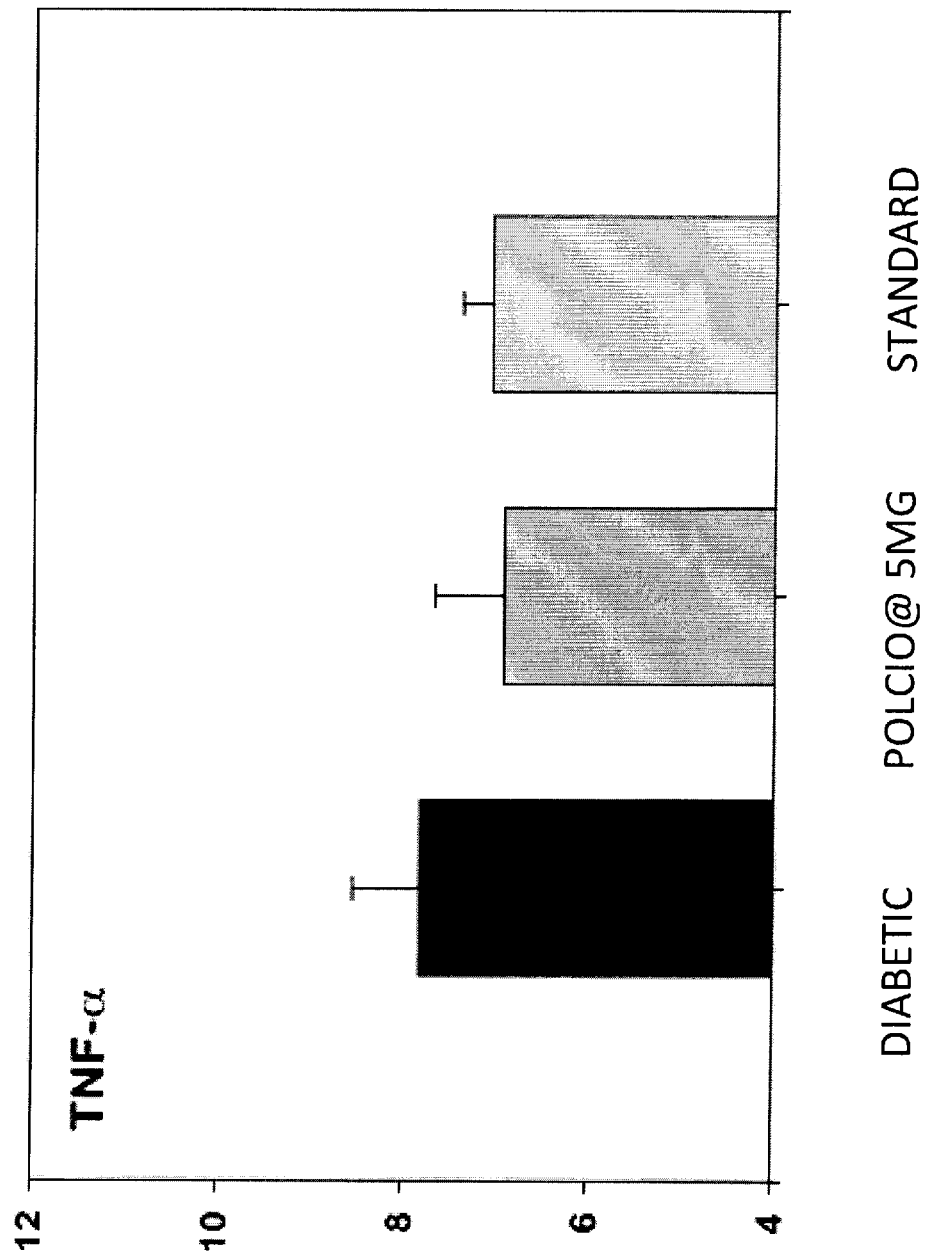
FIG. 23 shows TNF-alpha (tumor necrosis factor) levels in untreated rats and rats treated with particles of the invention.
Figure 24:
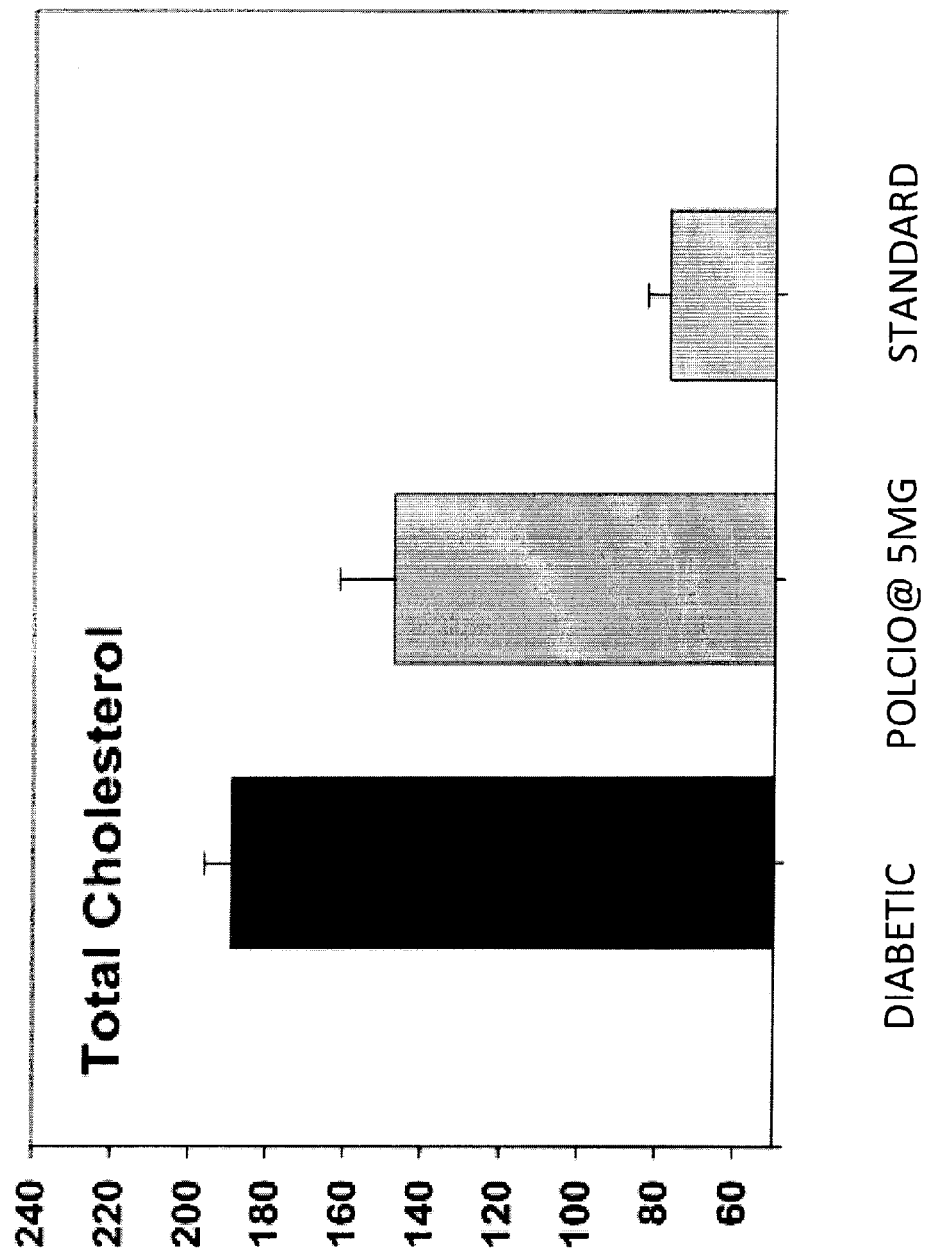
FIG. 24 shows total cholesterol levels in untreated rats and rats treated with particles of the invention.
Figure 25:
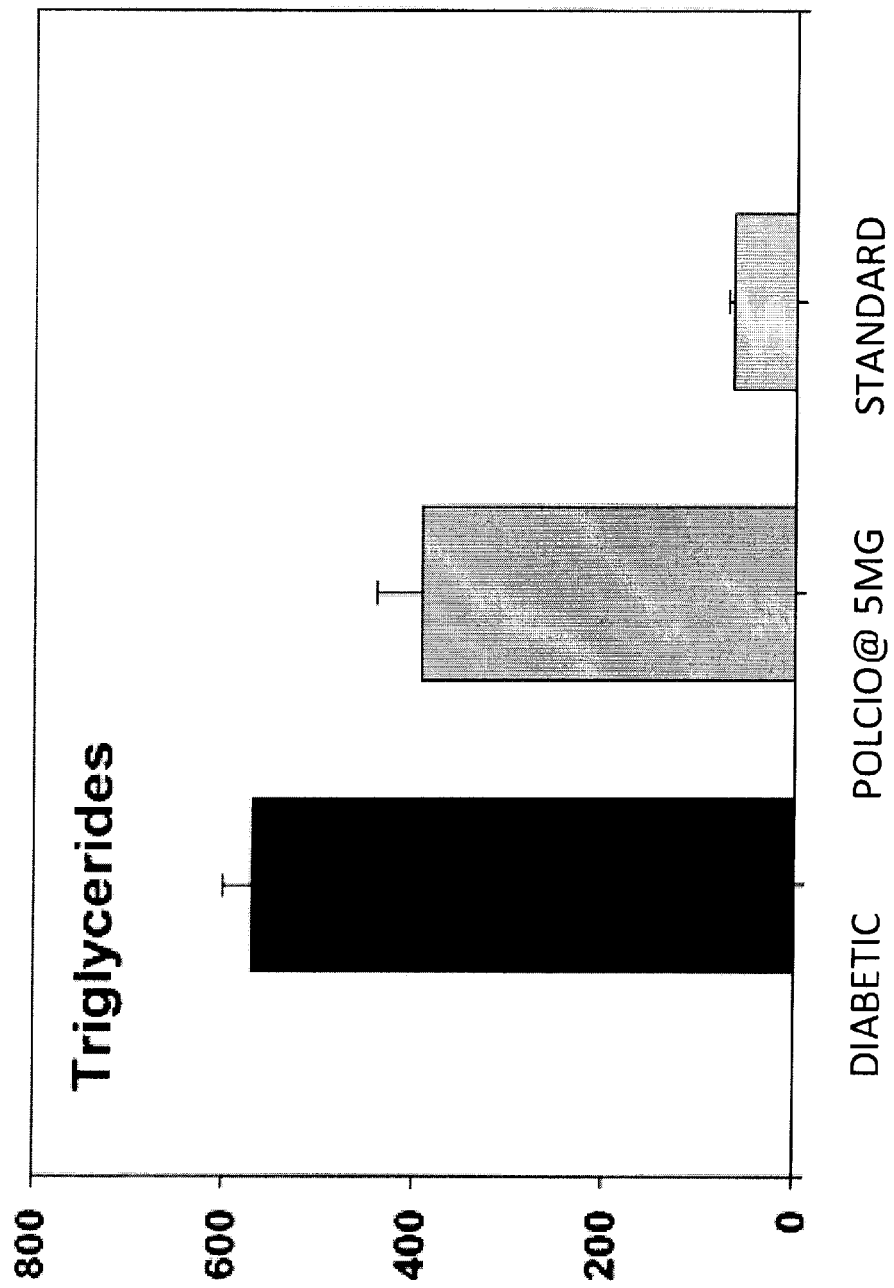
FIG. 25 shows triglyceride levels in untreated rats and rats treated with particles of the invention.
Figure 26:
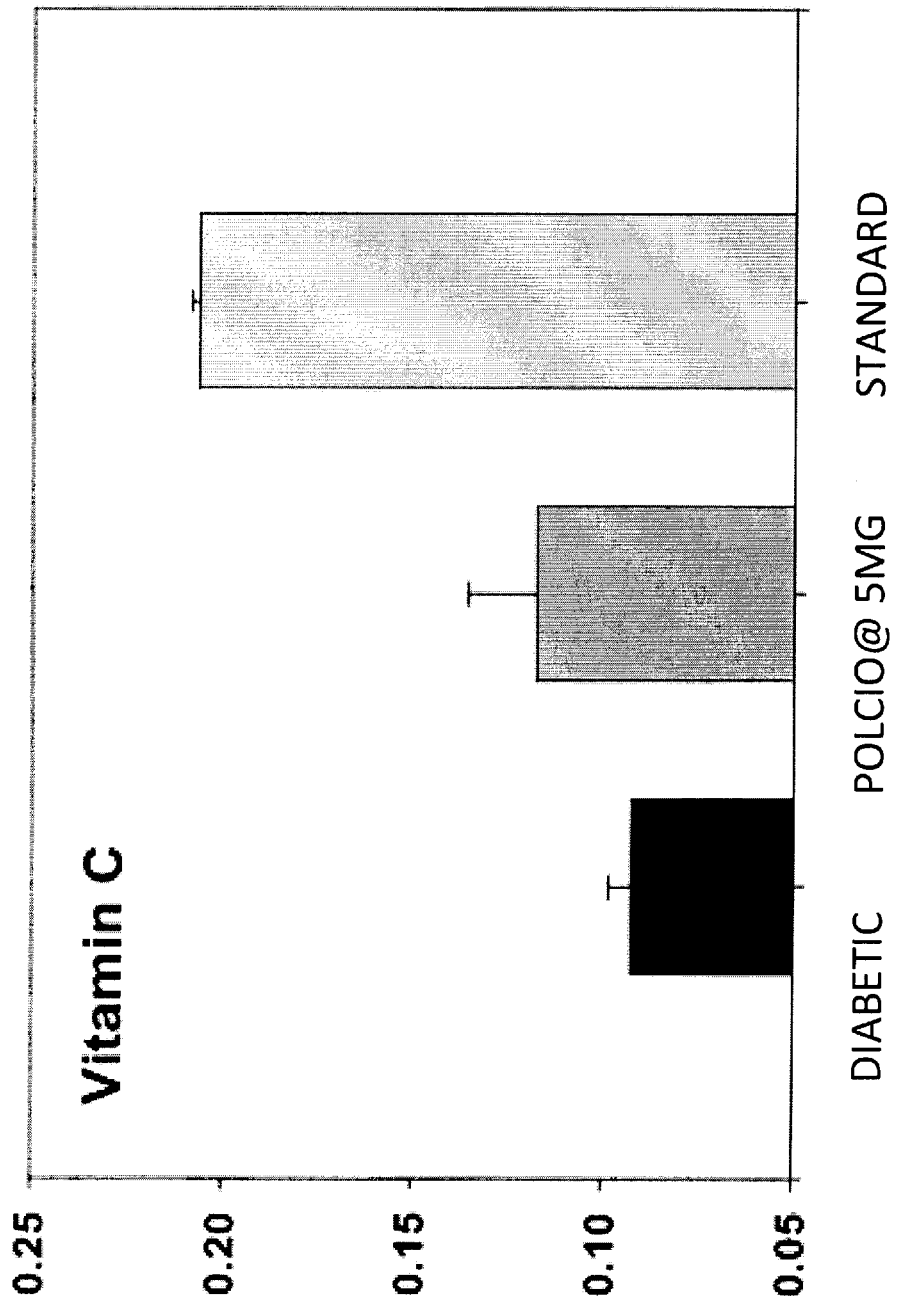
FIG. 26 shows vitamin-C levels in untreated rats and rats treated with particles of the invention.

Unless defined otherwise, all technical and scientific terms used herein generally have the same meaning as commonly understood by one of ordinary skill in the art to which this invention belongs.

The term "policosanol" refers to a mixture of concentrated N-alkyl alcohols. Exemplary sources of policosanol are sugar cane and bees wax. The policosanols are extracted by known methods. The long chain alcohols in policosanol are primarily 1-Octacosanol, 1-Triacontanol, 1-Tetracosanol, and 1-Hexacosanol. Typical commercially available commercial compositions are composed of 90% minimum fatty alcohols of (a) 1-Tetracosanol: 0-10%; (b) 1-Hexacosanol: 2-15%; (c) 1-Heptacosanol: 0-0.5%; (d) 1-Octacosanol: 55-70%; (e) 1-Nonacosanol: 0-10%; (f) 1-Triacontanol: 5-20%; (g) 1-Dotriacontanol: 0.1-10%; and (h) 1-Tetratriacontanol: 0.1-10%.

The terms "effective average particle size," "particle size" and "size" are used interchangeably. The terms refer to the particle size essentially corresponding to the apex of a peak produced in an assessment of particle size using light scattering. Useful methods for determining the size of the particles of the invention are not limited to light scattering.

The methods and formulations may be used for prophylactic or therapeutic purposes. In some embodiments, the terms "treating" or "treatment" of any disease or disorder refers to ameliorating the disease or disorder (i.e., arresting or reducing the development of the disease or at least one of the clinical symptoms thereof). In other embodiments, "treating" or "treatment" refers to ameliorating at least one physical parameter, which may not be discernible by the subject. In yet other embodiments, "treating" or "treatment" refers to inhibiting the disease or disorder, either physically, (e.g., stabilization or eradication of a discernible symptom), physiologically, (e.g., stabilization or eradication of a physical parameter) or both. In still other embodiments, "treating" or "treatment" refers to delaying the onset of the disease or disorder.

"Therapeutically effective amount" is used interchangeably herein with "an amount effective to," when referring to a method of the invention. When used in reference to a policosanol dosage, these terms refer to a dosage that provides the specific pharmacological response for which the policosanol is administered in a significant number of subjects in need of such treatment. It is emphasized that "therapeutically effective amount," administered to a particular subject in a particular instance may not be effective for 100% of patients treated for a specific disease, and will not always be effective in treating the diseases described herein, even though such dosage is deemed a "therapeutically effective amount" by those skilled in the art. It is to be further understood that policosanol dosages are, in particular instances, measured as oral dosages, or with reference to drug levels as measured in blood.

As used herein, the terms "individual," "subject," and "patient," are used interchangeably to refer to an animal, e.g. a mammal, e.g., a human.

A. The Compositions

In various embodiments, the invention provides a nanoparticle of policosanol. A representative nanoparticle of the invention includes a policosanol fraction comprising about 70% to 90% octacosanol; and a stabilizer fraction. In an exemplary embodiment, the stabilizer fraction includes a poly (ethylene glycol) ester. In various embodiments, the stabilizer fraction includes a tocopheryl ester. Exemplary components of the stabilizer fraction include tocopheryl poly (ethylene glycol) esters, e.g., tocopheryl polyethylene glycol (1000) succinate ("TPGS"). Exemplary nanoparticles of the invention have a diameter of less than about 100 nm. Also provided are formulations incorporating a plurality of the nanoparticles of the invention, including pharmaceutical formulations.

In various embodiments, the nanoparticles include a policosanol fraction that includes at least about 70% octacosanol, at least about 71% octacosanol, at least about 72% octacosanol, at least about 73% octacosanol, at least about 74% octacosanol, at least about 75% octacosanol, at least about 76% octacosanol, at least about 77% octacosanol, at least about 78% octacosanol, at least about 79% octacosanol, at least about 80% octacosanol, at least about 81% octacosanol, at least about 82% octacosanol, at least about 83% octacosanol, at least about 84% octacosanol, at least about 85% octacosanol or at least about 86% octacosanol, at least about 87% octacosanol, at least about 88% octacosanol, at least about 89% octacosanol, or at least about 90% octacosanol.

In various embodiments, the nanoparticles include a policosanol fraction that includes not more than about 90% octacosanol, not more than about 89% octacosanol, not more than about 88% octacosanol, not more than about 87% octacosanol, not more than about 86% octacosanol, not more than about 85% octacosanol, not more than about 84% octacosanol, not more than about 83% octacosanol, not more than about 82% octacosanol, not more than about 81% octacosanol, not more than about 80% octacosanol, not more than about 79% octacosanol, not more than 78% octacosanol, not more than 77% octacosanol, not more than 76% octacosanol, not more than 75% octacosanol, not more than 74% octacosanol, not more than 73% octacosanol, not more than 72% octacosanol, or not more than 71% octacosanol.

In an exemplary embodiment, the nanoparticles include a policosanol fraction having octacosanol in the range from about 70% to about 90%, from about 71% to about 89%, from about 72% to about 88%, from about 73% to about 87%, from about 74% to about 86%, from about 75% to about 85%, from about 76% to about 84%, from about 77% to about 83%, from about 78% to about 82%, from about 79% to about 81%, or about 80%.

In various embodiments, the policosanol fraction includes both octacosanol and triacontanol. In an exemplary embodiment, the policosanol used has an octacosanol-triacontanol ratio from about 8:1 to about 17:1, from about 9:1 to about 16:1, from about 10:1 to about 15:1, from about 11:1 to about 14:1, from about 12:1 to about 13:1, from about 8:1 to about 15:1, from about 8:1 to about 13:1, from about 8:1 to about 11:1, or from about 8:1 to about 9:1.

In various embodiments, the policosanol fraction includes both octacosanol and hexacosanol. In an exemplary embodiment, the policosanol used has an octacosanol:hexacontanol ratio ranging from about 16:1 to about 50:1; from about 18:1 to about 45:1; from about 19:1 to about 40:1; from about 19:1 to about 35:1; from about 19:1 to about 30:1; from about 19:1 to about 25:1; from about 19:1 to about 22:1; or from about 19:1 to about 20:1.

In various embodiments, the policosanol fraction includes both triacontanol and hexacosanol. In an exemplary embodiment, the policosanol used has a triacosanol:hexacontanol ratio of at most about 1.5:1, at most about 1.3:1; at most about 1:1; at most about 0.8:1; at most about 0.6:1; at most about 0.4:1; or at most about 0.2:1.

In an exemplary embodiment, the nanoparticles include a policosanol fraction that includes from 70% to about 95% octacosanol in admixture with triacontanol at a ratio of about 9:1 to about 16:1 and a stabilizer fraction that is essentially completely formed from TPGS (e.g., at least about 90%, 91%, 92%, 93%, 94%, 95%, 96%, 97% 98% or 99% TPGS). In various embodiments, the policosanol fraction and TPGS are in a ratio of about 1:2.8.

The present invention makes use of policosanol or a component of policosanol acquired or isolated from any appropriate source. For example, U.S. Pat. Nos. 5,663,156; 5,856,316; 6,197,832; 6,225,354; and 6,596,776, all of which are incorporated herein by reference, disclose policosanol compositions that are specific to the starting material and extraction processes used. In various embodiments, the policosanol of use in making a nanoparticle of the invention includes at least about 80% octacosanol, at least about 81% octacosanol, at least about 82% octacosanol, at least about 83% octacosanol, at least about 84% octacosanol, at least about 85% octacosanol, at least about 86% octacosanol, at least about 87% octacosanol, at least about 88% octacosanol, at least about 89% octacosanol or at least about 90% octacosanol. In various embodiments, the policosanol used includes between about 80% and about 85% octacosanol. In an exemplary embodiment, the amount of octacosanol is from about 82% to about 83%.

Various exemplary surfactants of use as a stabilizer fraction in the nanoparticle of the invention and its formulations include vitamin E TPGS (tocopherol propylene glycol succinate, a water-soluble form of vitamin E), sorbitan monolaurate (Span 20), sorbitan monopalmitate (Span 40), poloxamer, sorbitan monostearate (Span 60), sorbitan monooleate (Span 80), polyoxyethylene (20) sorbitan monolaurate (Tween 20, polysorbate 20), polyoxyethylene (20) monopalmitate (Tween 40, polysorbate 40), polyoxyethylene (20) monostearate (Tween 60, polysorbate 60), polyoxyethylene (20) tri-stearate (Tween 65, polysorbate 65), polyoxyethylene (20) monooleate (Tween 80, polysorbate 80), sucrose monomyristate, sucrose palmitate/stearate, sucrose stearate, dioctylsulfosuccinate sodium salt, monoglyceride monooleate, monoglyceride monolaurate, monoglyceride monopalmitate, lecithin, diglyceride mixtures, citric acid esters of monoglycerides, acetic acid esters of monoglycerides, lactic acid esters of monoglycerides, diacetyl tartaric esters of monoglycerides, polyglycerol esters of fatty acids, cyclodextrins, propylene glycol esters of fatty acids, stearoyl lactylates, $C_{8-18}$ free fatty acids, PTS (U.S. Pat. No. 6,045,826) or combinations thereof. In various embodiments, the stabilizer fraction does not include a cyclodextrin. In other embodiments, the stabilizer fraction does not include a polyoxyethylene sorbitan fatty acid ester.

The nanoparticles of the invention can include any useful ratio of policosanol fraction to stabilizer fraction that provides a nanoparticle having a diameter of less than or equal to about 100 nm. In an exemplary embodiment, the ratio of policosanol fraction:stabilizer fraction is from about 1:1 to about 1:4, for example, from about 1:2 to about 1:3.5. Similarly, in various embodiments, the ratio of octacosanol:stabilizer ranges from about 1:1.6 to about 1:2.8, for example, from about 1:2 to about 1:2.5. In an exemplary embodiment, the ratio is about 1:2.25. The ratio of triacontanol:stabilizer in exemplary nanoparticles of the invention ranges from about 1:10 to about 1:40, for example, from about 1:11: to about 1:35. In an exemplary embodiment, the stabilizer is an ester of vitamin E, such as TPGS (d-alpha-tocopheryl polyethylene glycol 1000 succinate).

The mixture from which the nanoparticles are produced can also include a surfactant in addition to the stabilizer fraction. Exemplary surfactants are set forth above and are generally known to those of skill in the art, e.g., TWEEN 20, TWEEN 80, esters (e.g., sucrose esters of palmitate and stearic acid monoesters), pectin, agar and the like.

The resultant nanoparticulate policosanol formulation can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

Nanoparticles and pharmaceutical formulations according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Exemplary excipient(s) that can be used in a nanoparticle or a formulation of the nanoparticles include, but are not limited to, soybean lecithin, soybean lecithin derivatives, caprylocaproyl macrogol-8 glycerides, medium chain triglycerides, refined olive oil, liquid flavors, polyoxyethylene sorbitan fatty acid esters, sugar esters, polyoxyethylene alkyl ethers, propylene glycol, dexpanthenol, almond oil, rice oil, sunflower oil, soybean oil, sesame oil, glycerin, glyceryl palmitostearate, sweet almond oil, oleic acid, polyglyceryl oleate, saccharose, poloxamer, macrogol-15 hydroxystearate, sorbitan fatty acid ester, ascorbyl palmitate, polethylene glycol, ceralution F, ceralution H, ceralution C, lauroyl macrogol-32 glycerides, glycerides, $C_{12}$-$C_{18}$ mono-, di- and triglycerides, glyceryl stearate, propylene glycol laureate, propyleen glycol caprylate, propylene glycol dipergonate. In some embodiments, the formulation includes one or more excipients selected from citric acid anhydrous, potassium sorbate, sodium benzoate, and sucrose laureate.

Examples of filling agents are lactose monohydrate, lactose anhydrous, and various starches; examples of binding agents are various celluloses and cross-linked polyvinylpyrrolidone, microcrystalline cellulose, such as Avicel™, PH101 and Avicel™ PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil™200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet™ (trademark of MAFCO), bubble gum flavor, and fruit flavors, and the like.

Examples of preservatives are potassium sorbate, methylparaben, propylparaben, benzoic acid and its salts, other esters of para hydroxybenzoic acid such as butylparaben, alcohols such as ethyl or benzyl alcohol, phenolic compounds such as phenol, or quaternary compounds such as benzalkonium chloride. Exemplary preservatives include, but are not limited to, potassium nitrite, sodium nitrite, benzoic acid, sodium benzoate, potassium benzoate and calcium benzoate Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel™ PH101 and Avicel™ PH102; lactose such as lactose monohydrate, lactose anhydrous, and Pharmatose™ DCL21; dibasic calcium phosphate such as Emcompress™; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In various embodiments, the compositions of the invention contain nanoparticulate policosanol nanoparticles, which have an average particle size of less than about 100 nm, less than about 90 nm, less than about 80 nm, less than about 70 nm, less than about 60 nm, or less than about 50 nm, as measured by light-scattering methods, microscopy, or other appropriate methods.

In one embodiment of the invention, there is provided a formulation in which at least 99% of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least 95% of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 90% of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 85% (e.g., from about 85% to about 99%, 95%, or 90%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 80% (e.g., from about 80% to about 99%, 95%, 90%, or 85%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 75% (e.g., from about 75% to about 99%, 95%, 90%, 85%, or 80%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 70% (e.g., from about 70% to about 99%, 95%, 90%, 85%, 80%, or 70%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 65% (e.g., from about 65% to about 99%, 95%, 90%, 85%, 80%, 75%, or 70%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 60% (e.g., from about 60% to about 99%, 95%, 90%, 85%, 80%, 75%, or 65%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least 55% (e.g., from about 55% to about 99%, 95%, 90%, 85%, 80%, 75%, 70%, 65%, or 60%) of the policosanol nanoparticles have a particle size less than about 100 nm, less than about 90 nm, less than about 80 nm, less than about 70 nm, less than about 60 nm, or less than about 50 nm, when measured by the above-mentioned methods.

Methods to determine the size of the nanoparticle are well known in the art. For example, optical diffraction (i.e. optical scatterometry) techniques can be used. These techniques include broadband scatterometry (U.S. Pat. Nos. 5,607,800; 5,867,276 and 5,963,329), spectral ellipsometry (U.S. Pat. No. 5,739,909) as well as spectral and single-wavelength beam profile reflectance and beam profile ellipsometry (U.S. Pat. No. 6,429,943). In addition it may be possible to employ single-wavelength laser BPR or BPE to obtain CD measurements on isolated lines or isolated vias and mesas (See U.S. patent application Ser. No. 10/243,245, filed Sep. 13, 2002).

In an exemplary embodiment, the invention provides a unit dosage formulation of policosanol nanoparticles of the invention containing a therapeutically effective amount of policosanol. In an exemplary embodiment, the unit dosage formulation is a formulation of nanoparticles containing a policosanol fraction and a stabilizer fraction and the unit dosage formulation includes from about 10 mg to about 100 mg, for example from about 10 mg to about 50 mg. In various embodiments, the unit dosage is a daily dosage. One of ordinary skill will appreciate that therapeutically effective amounts of policosanol can be determined empirically and can be employed in pure form or, where such forms exist, in pharmaceutically acceptable salt, ester, or pro-drug form. Actual dosage levels of policosanol in the nanoparticulate compositions of the invention may be varied to obtain an amount of the policosanol that is effective to obtain a desired therapeutic response for a particular composition and method of administration. The selected dosage level therefore depends upon the desired therapeutic effect, the route of administration, the potency of the administered policosanol, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

In an exemplary method for making a nanoparticle of the invention, a pre-selected quantity of a stabilizer and policosanol are melted together with stirring to ensure homogeneity. Water or an aqueous solution of an additive, preservative, excipient, etc. at an elevated temperature is added to the melt, and maintained at a desired temperature, generally from about 60° C. to about 90° C. while stirring. In an exemplary method, the mixture of water to solids includes more water than solids, e.g., is approximately 10:1 by weight. The mixture is stirred while cooling to room temperature. In various embodiments, the method produces a suspension of the particles A. The Methods In addition to nanoparticles of policosanol and formulations including these nanoparticles, the present invention provides methods of using these nanoparticles and formulations to treat and prevent disease and to regulate metabolism. In various embodiments, the nanoparticles of the invention are of use to regulate hypertension, cholesterol metabolism and treat hyperlipidemia, hypercholesterolemia, inflammation, etc. In various embodiments, the formulations are use to regulate or reduce protein oxidation. In an exemplary embodiment, the formulation are of use to manage glycemic levels, insulin resistance, diabetes, and other conditions related to blood sugar levels. In still further embodiments, the formulations are of use to regulate, e.g., increase, plasma vitamin C levels and to reduce systolic and diastolic blood pressure. In other embodiments, the formulations are of use to inhibit the activation of NF-κB.

In an exemplary embodiment, the formulations are administered in a therapeutically effective amount to a subject to treat a particular disease or disorder and wherein the subject is not otherwise in need of treatment with a policosanol. In various embodiments, the nanoparticles are administered to treat a single disease or regulate a single metabolic factor. Thus, in an exemplary embodiment, the invention provides a method to treat insulin resistance in a subject not in need of treatment for hyperlipidemia, hypercholesterolemia, hypertension, etc. In an exemplary embodiment, the invention provides a method of regulating blood sugar in a subject not in need of treatment for hyperlipidemia, hypercholesterolemia, etc. In various embodiments, the invention provides a method of treating diabetes (e.g., Type II diabetes) in a subject not in need of treatment for hyperlipidemia, hypercholesterolemia, etc. In various embodiments, the invention provides a method to decrease or prevent protein oxidation in a subject who is not in need of treatment for treatment for hypertension, hyperlipidemia, hypercholesterolemia, etc. In an exemplary embodiment, the invention provides a method of increasing serum vitamin C levels in a subject not in need of treatment for hyperlipidemia, hypercholesterolemia, etc. In other embodiments, the invention provides a method of inhibiting the activation of NF-κB in a subject not in need of treatment for hyperlipidemia, hypercholesterolemia, etc.

Non-limiting examples of methods of the invention are set forth below:

Protein Oxidation

The invention provides a method of decreasing protein oxidation in a subject and, therefore, reducing the deleterious consequences of this oxidation. The method includes administering to a subject a therapeutically effective amount of a policosanol formulation of the invention to decrease protein oxidation in a subject.

Oxidative stress has been implicated in the pathogenesis of acute and chronic diseases and injury in a variety of pathophysiological conditions such as hepatotoxin exposures, intrahepatic cholestasis, alcoholic liver injury, liver ischemia/reperfusion injury and viral hepatitis (Stehbens, *Exp. Mol. Pathol;* 2003; 75(3): 265; Jaeschke et al., *Toxicol. Lett.;* 2003; 144(3): 279-88; McDonough, *Toxicology.* 2003; 189(1-2): 89; Jaeschke et al., *J. Clin. Invest;* 1988; 81(4): 1240). Overproduction of reactive oxygen species (ROS) and nitrogen species (RNS), along with significant decrease of antioxidant defense in these pathological conditions, impairs various cellular functions through the processes of lipid peroxidation, protein oxidation and nucleic base oxidation. Lipid peroxidation, for example, causes changes in the physical and chemical properties of cellular membranes, thus altering their fluidity and permeability, leading to impairment in membrane signal transduction and ion exchange, resulting in swelling, cytolysis and finally cell death. The oxidation of proteins and DNA also relates directly to cellular dysfunction and death (Fang Y Z et al. *Nutrition.* 2002; 18(10): 872-9).

Diseases related to protein oxidation include, but are not limited to, rheumatoid arthritis (IgG, α-1-proteinase inhibitor), ischemia reperfusion injury, emphysema (α-1-proteinase inhibitor, elastase), neurodegenerative diseases (e.g., Alzheimer, Parkinson's), muscular dystrophy, disorders associated with aging (glutamine synthetase, carbonic anhydrase III, aconitase), acute pancreatitis, cataractogenesis (α-crystallins), cancer, chronic ethanol ingestion, adult respiratory distress syndrome. The formulations of the invention can also be used to treat or ameliorate the effects of Kwashikor (Manory, *J. Pediatr;* 2000; 137: 421).

An exemplary therapeutically relevant dose is one that leads to a reduction in a standard clinical marker of protein oxidation, e.g., protein carboxylation. Protein carbonyl content (PCC) is the most widely used marker of oxidative modification of proteins. There are several methodologies for the quantitation of PCC; in various conventional methods, 2,4-dinitrophenyl hydrazine is allowed to react with the protein carbonyls to form the corresponding hydrazone, which can be analyzed optically by radioactive counting or immunohistochemically. See, e.g., Yan et al., *Arch. Biochem. Biophys.* 327:330-334, 1996.

In various embodiments, the nanoparticles of the invention are administered orally. In an exemplary embodiment, the nanoparticles are administered at a dosage of from about 10 mg to about 100 mg per day, for example, from about 10 mg to about 50 mg per day.

Increase in Serum Vitamin C

The invention also provides a method of increasing serum vitamin C in a subject. The method includes administering to a subject a therapeutically effective amount of a policosanol formulation of the invention to increase or regulate serum vitamin C levels in a subject.

Because insulin resistance and diabetes are accompanied by decreased serum vitamin C levels as compared to the levels observed in healthy subjects, orally administered supplemental vitamin C has been suggested as a treatment for the consequences of insulin resistance and diabetes, including endothelial dysfunction. However, supplemental vitamin C was not found to be effective when used alone (Kaneto et al., *Diabetes;* 1999; 48(12): 2398), quite possibly because orally administered vitamin C supplements does not improve endothelial dysfunction or insulin resistance (Chen et al., *Am. J. Physiol. Heart Circ. Physiol.;* 2006; 290(1): H137).

The present invention provides a method of regulating endogenous vitamin C and, therefore, a method of treating insulin resistance, diabetes and the consequences of these syndromes.

An exemplary therapeutically relevant dose is one that leads to an increase in a standard clinical marker of serum Vitamin C concentration, e.g., a sandwich ELISA method using commercially available kits from Fisher Thermo Scientific Co, Rockford, Ill. See, e.g., Washko et al., *Anal. Biochem.* 1992; 204:1-14.

In various embodiments, the nanoparticles of the invention are administered orally. In an exemplary embodiment, the nanoparticles are administered at a dosage of from about 10 mg to about 100 mg per day, for example, from about 10 mg to about 50 mg per day.

Insulin Resistance

The present invention also provides a method of treating insulin resistance and the consequences arising out of insulin resistance including, but not limited to, diabetes. The method includes administering to a subject an amount of a particulate formulation of the invention sufficient to treat insulin resistance.

Insulin resistance is defined as an inadequate response by insulin target tissues, such as skeletal muscle, liver, and adipose tissue, to the physiologic effects of circulating insulin. The hallmarks of impaired insulin sensitivity in these three tissues are decreased insulin-stimulated glucose uptake into skeletal muscle, impaired insulin-mediated inhibition of hepatic glucose production in liver, and a reduced ability of insulin to inhibit lipolysis in adipose tissue. In fact, insulin resistance is a major predictor for the development of Type II diabetes.

In Type II diabetes, it has been widely established that insulin resistance precedes the development of overt hyperglycemia. The causes of insulin resistance can be genetic and/or acquired. Type II diabetes also predisposes patients to elevated cholesterol and cardiovascular disease. In Western cultures, the most common acquired factors causing insulin resistance are obesity, sedentary lifestyle, and aging, all of which are interrelated. In the presence of a robust compensatory insulin secretory response to insulin resistance, glucose levels can remain relatively normal. However, when insulin-producing pancreatic β cells can no longer compensate for the decreased tissue insulin sensitivity, glucose homeostasis deteriorates and impaired glucose tolerance and eventually Type II diabetes develop.

Individuals suffering from diabetes also have decreased levels of vitamin C in the bloodstream. Studies have found that diabetics have at least 30% lower circulating ascorbic acid levels than normal individuals. (Will et al., *Nutr. Rev.*

54(7): 193 (1996)). However, administering high-dose oral vitamin C does not ameliorate this deficiency. (Chen et al., *J. Physiol. Heart Circ. Physiol.,* 290(1):H137-45 (2006)). However, as will be seen in the Examples below, the administration of the present invention addresses this deficiency.

Common diseases or disorders associated with insulin resistance include acanthosis nigricans, acne vulgaris, allergies, asthma, Alzheimer's Disease, atherosclerosis, bipolar disorder, breast cancer, cardiovascular disease, cataracts, cervical cancer, depression, diabetes mellitus, dyslipidemia, fatty liver disease, childhood Type-2 diabetes, chronic fatigue, colon and rectal cancer, dandruff, Graves' disease, heart disease, high LDL cholesterol, high triglycerides, hirsutism, hypoglycemia, hypothyroidism, inflammation, kidney disease, low HDL cholesterol, lupus, neuropathy, neuritis, osteoporosis, pancreatic cancer, Parkinson's disease, polycystic ovary syndrome, prostate cancer, rheumatoid arthritis, scleroderma, seborrhea, strokes, and varicose veins.

In addition to the diseases and disorders set forth above, some of the main consequences of insulin resistance include, but are not limited to, Type 2 diabetes mellitus, hypertension, arteriosclerosis, polycystic ovarian syndrome, non-alcoholic fatty liver disease, disturbances in the function of the vascular endothelium, elevation of triglycerides and cholesterol, disturbances of clotting, disturbances in kidney function, disturbances in heart rhythm, and elevated uric acid levels.

An exemplary therapeutically relevant dose is one that leads to a decrease in a standard clinical marker of serum insulin resistance, e.g., insulin and insulin levels in the plasma can be determined by the sandwich ELISA method using commercially available kits from Fisher Thermo Scientific Co, Rockford, Ill.).

In various embodiments, the nanoparticles of the invention are administered orally. In an exemplary embodiment, the nanoparticles are administered at a dosage of from about 10 mg to about 100 mg per day, for example, from about 10 mg to about 50 mg per day.

Cholesterol-Related Diseases

In various embodiments, the present invention provides a method of treating hypercholesterolemia and/or regulating lipid metabolism in a subject. The method includes administering to a subject an amount of a nanoparticulate formulation of the invention sufficient to treat hypercholesterolemia.

Hypercholesterolemia, hyperlipidemia and cardiovascular disease are increasingly prevalent in Western industrial societies. The reasons for this are not completely understood, but may relate partly to a genetic predisposition to these conditions and partly to a diet high in saturated fats, together with an increasingly sedentary lifestyle as manual labor becomes increasingly less necessary. Hypercholesterolemia and hyperlipidemia are very significant, because they predispose individuals to cardiovascular disease, including atherosclerosis, myocardial infarction (heart attack), and stroke.

Specific forms of hyperlipidemia include, for example, hypercholesterolemia, familial dysbetalipoproteinemia, diabetic dyslipidemia, nephrotic dyslipidemia and familial combined hyperlipidemia. Hypercholesterolemia is characterized by an elevation in serum low-density lipoprotein-cholesterol and serum total cholesterol. Low-density lipoprotein (LDL cholesterol) transports cholesterol in the blood. Familial dysbetalipoproteinemia, also known as Type III hyperlipidemia, is characterized by an accumulation of very low-density lipoprotein-cholesterol (VLDL-cholesterol) particles called beta VLDLs in the serum. Also associated with this condition is a replacement of normal apolipoprotein E3 with abnormal isoform Apo lipoprotein E2. Diabetic dyslipidemia is characterized by multiple lipoprotein abnormalities, such as an overproduction of VLDL-cholesterol, abnormal VLDL triglyceride lipolysis, reduced LDL-cholesterol receptor activity and, on occasion, Type III hyperlipidemia. Nephrotic dyslipidemia, associated with malfunction of the kidneys, is difficult to treat and frequently includes hypercholesterolemia and hypertriglyceridemia. Familial combined hyperlipidemia is characterized by multiple phenotypes of hyperlipidemia, i.e., Type IIa, IIb, IV, V or hyperapobetalipoproteinemia.

It is well known that the likelihood of cardiovascular disease can be decreased if the serum lipids, and in particular LDL-cholesterol, can be reduced. It is also well known that the progression of atherosclerosis can be retarded or the regression of atherosclerosis can be induced if serum lipids can be lowered. In such cases, individuals diagnosed with hyperlipidemia or hypercholesterolemia should consider lipid-lowering therapy to retard the progression or induce the regression of atherosclerosis for purposes of reducing their risk of cardiovascular disease, and in particular coronary artery disease. Such therapy will reduce the risk of stroke and myocardial infarction, among other consequences. In addition, certain individuals with what are considered normal serum lipid levels can develop cardiovascular disease. In these individuals other factors like lipid peroxidation and high levels of Lp(a) or lipoprotein A can lead to atherogenesis despite relatively normal cholesterol and lipid levels.

Exemplary markers of a "therapeutically effective amount" as used herein refers to the amount of policosanol in a formulation of the invention which, upon administration (e.g., oral administration) to the subject, maintains healthy serum lipid profiles, illustratively by lowering total cholesterol levels, lowering LDL cholesterol, raising HDL cholesterol, lowering the total cholesterol/HDL ratio, and/or lowering triglycerides, or aids in maintaining a healthy body weight.

Another exemplary therapeutically relevant dose is one that leads to a decrease of C-Reactive Protein, a standard clinical marker of lipid metabolism and cardiovascular risk factor.

Inhibition of NF-κB Activation

In various embodiments, the present invention provides a method of inhibiting the activation of NF-κB in a subject. The method includes administering to a subject an amount of a nanoparticulate formulation of the invention sufficient to inhibit the activation of NF-κB.

The NF-kB/Rel family of transcription factors is comprised of several structurally-related proteins that form homodimers and heterodimers and include p50/p105, p52/p100, RelA (p65), c-Rel/NF-kB. The most common Rel/NF-kB dimer in mammals contains p50-RelA (p50/p65) heterodimers and is specifically called NF-kB. It is a ubiquitous factor that resides in the cytoplasm but, when activated, it is translocated to the nucleus, where it induces gene transcription. NF-kB has been linked to a wide variety of diseases, because most diseases are caused by unregulated inflammation. Thus, agents that can inhibit NF-kB activation have the potential to prevent or delay the onset of or treat NF-kB-linked diseases.

NF-kB is activated by free radicals, inflammatory stimuli, carcinogens, tumor promoters, endotoxin, gamma radiation, ultraviolet (UV) light, and x-rays (B. B. Aggarwal et al., Nuclear transcription factor-kappa B as a target for cancer drug development Leukemia. 16: 1053-68). On activation, NF-kB induces the expression of more than 200 genes that have been shown to suppress apoptosis, induce cellular transformation, proliferation, invasion, metastasis, chemo-resistance, radio-resistance, and inflammation. See Kumar A, et al., 2004. Nuclear factor-kappa B: Its role in health and diseases, J Mol. Med., 82:434-448.

The activated form of NF-kB has been implicated in diseases and disorders, including, without limitation: cancer, allergies, headaches, pain, myocardial infarctions, complex regional pain syndrome, cardiac hypertrophy, muscular dystrophy (type 2a), muscle wasting, catabolic disorders, type 1 diabetes, type 2 diabetes, obesity, fetal growth retardation, hypercholesterolemia, atherosclerosis, heart disease, chronic heart failure, ischemia/reperfusion, stroke, cerebral aneurysm, angina pectoris, pulmonary disease, cystic fibrosis, acid-induced lung injury, pulmonary hypertension, chronic obstructive pulmonary disease (COPD), hyaline membrane disease, kidney disease, glomerular disease, alcoholic liver disease, leptospiriosis renal disease, gut diseases, peritoneal endometriosis, skin diseases, nasal sinusitis, mesothelioma, anhidrotic ectodermal dysplasia, Behcet's disease, incontinentia pigmenti, tuberculosis, asthma, arthritis, Crohn's Disease, colitis (rat), ocular allergy, glaucoma, appendicitis, Paget's Disease, pancreatitis, periodontitis, endometriosis, inflammatory bowel disease, inflammatory lung disease, sepsis, silica-induced, sleep apnea, AIDS (HIV-1), autoimmunity, antiphospholipid syndrome, lupus, lupus nephritis, Waldenstrom macroglobulinemia, chronic disease syndrome, familial Mediterranean Fever, hereditary periodic fever syndrome, psychosocial stress diseases, neuropathological diseases, familial amyloidotic polyneuropathy, inflammatory neuropathy, traumatic brain injury, spinal cord injury, psoriasis, septic shock, Parkinson disease, multiple sclerosis, rheumatic disease, Alzheimer's disease, amyotrophic lateral sclerosis, Huntington's disease, retinal disease, cataracts, and various inflammatory diseases. The formulations and methods of the invention demonstrate the ability to inhibit activation of NF-kB, which can in turn treat or prevent diseases associated with NF-kB activation in the body.

Adiponectin

In various embodiments, the present invention provides a method of increasing adiponectin levels in a subject. The method includes administering to a subject an amount of a nanoparticulate formulation of the invention sufficient to increase adiponectin levels and thereby treat diseases associated with low adiponectin levels.

Adiponectin is a protein hormone that modulates a number of metabolic processes, including glucose regulation and fatty acid catabolism. See Díez J J, Iglesias P. "The role of the novel adipocyte-derived hormone adiponectin in human disease". Eur. J. Endocrinol. 148 (3): 293-300, 2003.

Adiponectin is exclusively secreted from adipose tissue into the bloodstream and is very abundant in plasma relative to many other hormones. Levels of the hormone are inversely correlated with body fat percentage in adults. See Ukkola O, Santaniemi, "Adiponectin: a link between excess adiposity and associated co-morbidities" J. Mol. Med. 80 (11): 696-702, 2002.

The hormone plays a role in the suppression of the metabolic derangements that may result in type 2 diabetes, obesity, atherosclerosis, non-alcoholic fatty liver disease (NAFLD) and an independent risk factor for metabolic syndrome. See Renaldi O. et al., 2009 "Hypoadiponectinemia: a risk factor for metabolic syndrome" Acta Med Indones 41 (1): 20-4.

Plasminogen Activation Inhibitor

In various embodiments, the present invention provides a method of regulating, e.g. lowering, the PAI-1 protein level in a subject. The method includes administering to a subject an amount of a nanoparticulate formulation of the invention sufficient to reduce the PAI-1 level in the subject. PAI-1 is a serine protease inhibitor that inhibits fibrinolysis by inactivating urokinase-type and tissue-type plasminogen activator. Plasma PAI-1 activity is highest between 12 midnight and 6 am. (Kluft C, et al., Thromb Haemost. 1988 Apr. 8; 59(2): 329-32).

PAI-1 is present in increased levels in various disease states (such as a number of forms of cancer), as well as in obesity and the metabolic syndrome. It has been linked to the increased occurrence of thrombosis in patients with these conditions. (Mimuro J (1991)"[Type 1 plasminogen activator inhibitor: its role in biological reactions]". Rinsho Ketsueki 32 (5): 487-9. PMID 1870265.): Binder B R, et al. (2002). "Plasminogen activator inhibitor 1: physiological and pathophysiological roles". News Physiol. Sci. 17: 56-61. PMID 11909993: Hoekstra T, et al., (2004). "Plasminogen activator inhibitor-type 1: its plasma determinants and relation with cardiovascular risk". Thromb. Haemost. 91 (5): 861-72: Lijnen H R (2005). "Pleiotropic functions of plasminogen activator inhibitor-1". J. Thromb. Haemost. 3 (1): 35-45; De Taeye B, et al., (2005). "Plasminogen activator inhibitor-1: a common denominator in obesity, diabetes and cardiovascular disease". Current opinion in pharmacology 5 (2): 149-54: Dellas C, Loskutoff D J (2005). "Historical analysis of PAI-1 from its discovery to its potential role in cell motility and disease". Thromb. Haemost. 93 (4): 631-40.

TNF Alpha

In various embodiments, the present invention provides a method of regulating, e.g. lowering, the TNF alpha levels in a subject. The method includes administering to a subject an amount of a nanoparticulate formulation of the invention sufficient to reduce the TNF alpha levels in a subject and thereby treat diseases associated with elevated TNF alpha levels. Tumor necrosis factor (TNF alpha) promotes the inflammatory response, which, in turn, causes many of the clinical problems associated with autoimmune disorders such as rheumatoid arthritis, ankylosing spondylitis, Crohn's disease, psoriasis, Alzheimer's and refractory asthma. These disorders are sometimes treated by using a TNF inhibitor. Dysregulation of TNF production has been implicated in a variety of human diseases including Alzheimer's (Perispinal Etanercept for Treatment of Alzheimer's Disease Edward Tobinick* Current Alzheimer Research, 2007, 4, 550-552) as well as cancer. See Locksley R M, Killeen N, Lenardo M J (2001). "The TNF and TNF receptor super families: integrating mammalian biology". Cell 104 (4): 487-501.

Obese rodents and obese humans have increased expression of TNF a in the adipose tissue. TNF α expression in adipose tissue thus positively correlates with adiposity and insulin resistance (Endocr Rev. 2003 June; 24(3): 278-301). Chronic exposure to exogenous TNF α in vivo and in vitro induces insulin resistance. See Endocrinology. 1992 January; 130(1):43-52 Gene deletion of TNF α or its receptors in obese rodents (fa/fa Zucker rats) improves insulin sensitivity and circulating NEFAs. Nature. 1997 Oct. 9; 389(6651):610-4

In the adipose tissue, TNF α suppresses genes involved in uptake and storage of NEFAs and glucose as well as adipogenesis. It also modifies expression of adipocyte-secreted factors as adiponectin (Am J Physiol Endocrinol Metab. 2003 September; 285(3):E527-33. In the liver, TNF α suppresses expression of the genes involved in glucose uptake and metabolism and fatty acid oxidation while increasing expression of genes involved in de novo synthesis of cholesterol and fatty acids.

Insulin signaling is indirectly impaired by TNF α through increased serum NEFA levels. Thiazolidinediones have been known to improve the inhibitory effects of TNF a on insulin action. See J Clin Invest. 1997 Oct. 1; 100(7):1863-9. Furthermore, weight loss has been observed to result in a decrease in TNF α levels. J Clin Invest. 1995 May; 95(5): 2111-9.

Retinol Binding Protein

In various embodiments, the present invention provides a method of regulating, e.g. lowering, the RBP-4 levels in a subject. The method includes administering to a subject an amount of a nanoparticulate formulation of the invention sufficient to reduce the RBP-4 levels in a subject and thereby treat diseases associated with elevated RBP-4 levels. Retinol binding protein 4 (RBP4) has recently been described as an adipokine that contributes to insulin resistance in the AG4KO mouse model. See Yang Q, et al., Serum retinol binding protein 4 contributes to insulin resistance in obesity and type 2 diabetes", Nature 436 (7049): 356-62. (2005). RBP4 is elevated in the serum before the development of diabetes and appears to identify insulin resistance and associated cardiovascular risk factors in subjects with varied clinical presentations. These findings provide a rationale for antidiabetic therapies aimed at lowering serum RBP4 levels. See Graham T E, et. al N Engl J. Med. 2006 Jun. 15; 354(24):2552-63.

Nitric Oxide

In various embodiments, the present invention provides a method of increasing nitric oxide levels in a subject. The method includes administering to a subject an amount of a nanoparticulate formulation of the invention sufficient to increase nitric oxide levels in a subject.

Endothelial NOS (eNOS), also known as nitric oxide synthase 3 (NOS3), generates NO in blood vessels and is involved with regulating vascular function and in reducing blood pressure. See Alderton W K, et al., Biochem J. 2001 Aug. 1; 357(Pt 3):593-615. NO is known to have various vascular effects, including direct vasodilatation (flow dependent and receptor mediated); indirect vasodilatation by inhibiting vasoconstrictor influences (e.g., inhibits angiotensin II and sympathetic vasoconstriction), anti-thrombotic effect (inhibits platelet adhesion to the vascular endothelium), anti-inflammatory effect (inhibits leukocyte adhesion to vascular endothelium), the ability to scavenge for superoxide anion; and anti-proliferative effect (e.g., inhibits smooth muscle hyperplasia).

Because of the above-mentioned actions of NO, its impaired production or reduced bioavailability can result in vasoconstriction (e.g., coronary vasospasm, elevated systemic vascular resistance, hypertension); thrombosis due to platelet aggregation and adhesion to vascular endothelium; inflammation due to up-regulation of leukocyte and endothelial adhesion molecules; vascular hypertrophy and stenosis. See Nitric Oxide: Biology and Pathobiology; By: Louis J. Ignarro (Editor) ISBN-10: 0123738660; ISBN-13: 9780123738660 Publisher: Academic Press—2009. Diseases or conditions associated with abnormal NO production and bioavailability include, without limitation, hypertension; obesity; dyslipidemias (particularly hypercholesterolemia and hypertriglyceridemia); diabetes (types I and II); heart failure; atherosclerosis; and conditions associated with aging. See Dessy, C, et al., (September 2004). "Pathophysiological Roles of Nitric Oxide: In the Heart and the Coronary Vasculature" and Current Medical Chemistry—Anti-Inflammatory & Anti-Allergy Agents in Medicinal Chemistry (Bentham Science Publishers Ltd.) 3 (3): 207-216.

MCP-1 (Monocyte Chemotactic Protein-1)

In various embodiments, the present invention provides a method of regulating, e.g. lowering, the MCP-1 levels in a subject. The method includes administering to a subject an amount of a nanoparticulate formulation of the invention sufficient to reduce the MCP-1 levels in a subject and thereby treat diseases associated with elevated MCP-1 levels. MCP-1 is a chemokine that recruits monocytes to sites of inflammation. MCP-1 is expressed and secreted by adipocytes and stromal vascular cells in white adipose tissue. Obese rodents have higher circulating MCP-1 levels with increased adipose tissue expression of MCP-1. See J Biol. Chem. 2003 Nov. 21, 278(47):46654-60. Furthermore, MCP-1 can directly contribute to insulin resistance by decreasing insulin stimulated glucose uptake and insulin induced insulin receptor tyrosine phosphorylation and can decrease the expression of adipogenic genes so as to inhibit adipocyte growth and differentiation.

Administration of MCP-1 to mice peripherally increases circulating monocytes, and increases monocyte accumulation in arteries with neo-intimal formation suggesting a role for MCP-1 in atherogenesis. See Cardiovasc Res. 2003 January; 57(1):178-85.

Hydrogen Sulfide

In various embodiments, the present invention provides a method of increasing $H_{2S}$ levels in a subject. The method includes administering to a subject an amount of a nanoparticulate formulation of the invention sufficient to increase serum $H_2S$ levels in a subject and thereby treat diseases associated with low $H_2S$ levels. $H_2S$ promotes a number of cellular signals that regulate metabolism, cardiac function and cell survival. Endogenous $H_2S$ bioavailability is regulated by several enzymes involved in the biosynthesis of cysteine. See Szabo C (2007). Hydrogen sulfide and its therapeutic potential. Nat Reviews 6: 917-935. Levels of $H_2S$ in blood samples taken from healthy people and male patients with type II diabetes demonstrated markedly decreased levels of H2S in the diabetes patients. Lower $H_2S$ levels were associated with clinical markers of impaired micro vessel function suggesting that a loss of this blood pressure lowering gas could be a contributing factor in the development of vascular complications in patients with diabetes. See Brancaleone V, et al., (2008). Biosynthesis of H2S is impaired in non-obese diabetic (NOD) mice; Br J Pharmacol 155: 673-680: Lefer D J (2007). A new gaseous signaling molecule emerges: cardio protective role of hydrogen sulfide; and Proc Natl Acad Sci USA 104: 17907-17908.

ICAM-1 (Inter Cellular Adhesion Molecule-1)

In various embodiments, the present invention provides a method of regulating, e.g. reducing, elevated ICAM-1 levels in a subject. The method includes administering to a subject an amount of a nanoparticulate formulation of the invention sufficient to reduce ICAM-1 levels in a subject and thereby treat diseases associated with elevated ICAM-1 levels. ICAM-1 is the same receptor molecule used by the vast majority of viruses that cause the common cold. Rhinoviruses are the frequent cause of the common cold. Adhesion molecules play a major role in many fields of medicine including embryology, immunology, and malignancy.

Many physiological processes require that cells come into close contact with and adhere to other cells or the extracellular matrix. Cell-cell and cell-matrix interactions are mediated through several families of intercellular adhesion molecules or "ICAMs." See New Cell adhesion research, Patrick Nott and other contributors, ISBN-10: 1606923781; ISBN-13: 9781606923788 Publisher: Nova Biomedical Books-2009-04. ICAM-1 therefore plays an essential role in both normal and pathophysiological processes (Springer et al., 1987, Ann. Rev. Immunol. 5: 223-252). Strategies have therefore been developed to mediate cell adhesion by blocking ICAM-1 function or expression. Such strategies typically employ anti-ICAM-1 antibodies, ligands which competitively block ICAM-1 binding, or antisense nucleic acid molecules directed against ICAM-1 mRNA. However, the agents used in such therapies produce only a stoichiometric reduction in ICAM-1, and are typically overwhelmed by the abnormally high production of ICAM-1 by the diseased or activated cells.

Diseases characterized by infiltration of neutrophils are often associated with chronic conditions wherein ICAM-1 or VCAM-1 expression predominates. See Adams D H, Shaw S 1994 Leukocyte endothelial interactions and regulation of leukocyte migration. Lancet 343:831-836. An increase in local expression as well as in serum-soluble adhesion molecules has been reported in diverse pathologic conditions including arteriosclerosis, vasculitis, arthritis, renal and hepatic diseases, ischemia reperfusion conditions, organ rejection, metastasis, and many more pathologic conditions. See Bevilacqua M P, et al., 1994 Endothelial leukocyte adhesion molecules in human disease. Annu Rev Med 45:361-378.

Adhesion molecules may be important in specific forms of inflammation. See Gorski A 1994 the role of cell adhesion molecules in immunopathology. Immunol Today 15:251-255. What is needed, therefore, are agents in catalytic or sub-stoichiometric amounts which selectively inhibit expression of ICAM-1, in order to effectively decrease or block ICAM-1-mediated cell adhesion.

One of the many different ways of inhibiting viral infection is to stop the virus from binding to cells. Most of the rhinovirus serotypes use a single cellular receptor, i.e. the Intercellular Adhesion Molecule-1 (ICAM-1) for attachment to the cells. This could lead to the development of blockers of this receptor in an effort to find a cure for the common cold.

Expression of ICAM-1 has also been associated with a variety of inflammatory skin disorders such as allergic contact dermatitis, fixed drug eruption, lichen planus, and psoriasis. See Ho et al., 1990, J. Am. Acad. Dermatol. 22: 64-68; Griffiths and Nickoloff, 1989, Am. J. Pathology 135: 1045-1053; Lisby et al., 1989, Br. J. Dermatol. 120: 479-484; and Shiohara et al., 1989, Arch. Dermatol. 125: 1371-1376. In addition, ICAM-1 expression has been detected in patients with rheumatoid arthritis (Hale et al., 1989, Arth. Rheum. 32: 22-30); in pancreatic B-cells of diabetics (Campbell et al., 1989, P.N.A.S. USA 86: 4282-4286); in thyroid follicular cells of patients with Graves' disease (Weetman et al., 1989, J. Endocrinol. 122: 185-191); in renal and liver allograft rejection (Faull and Russ, 1989, Transplantation 48: 226-230; Adams et al., 1989, Lancet 1122-1125); and in inflammatory bowel disease (IBD) tissue (Springer T, 1990, Nature 346: 425-34).

Complications commonly observed in type I diabetes also involve expression of ICAM-1. For example, ICAM-1-mediated adhesion of leukocytes to capillary endothelium can cause microvascular ischemia in certain tissues of diabetics, such as the retina, peripheral nerves, and kidney. This results in capillary non-perfusion of these tissues, which in turn leads to diabetic retinopathy, neuropathy or nephropathy, or angiogenesis induced by adhesion between polymorphonuclear leukocyte and endothelial cell via intercellular adhesion molecule-1, (ICAM-1). It is therefore believed that inhibition of ICAM-1-mediated leukostasis can prevent retinal abnormalities associated with diabetes. See Miyamoto K et al. (2000), Am. J. Pathol. 156: 1733-1739; Miyamoto K et al. (1999), P.N.A.S USA 96:10836-1084; Jude E B et al. (1998), Diabetologia 41:330-6; Miyamoto et al. 1999, P.N.A.S USA 96: 10836-10841; and Yong Song Gho et. al Cancer Research 59, 5128-5132, Oct. 15, 1999.

Glutathione

In various embodiments, the present invention provides a method of increasing or regulating GSH levels in a subject. The method includes administering to a subject an amount of a nanoparticulate formulation of the invention sufficient to increase or regulate GSH levels in a busject.

The reduced form of glutathione (GSH) is the most prevalent non-protein thiol in animal cells. Its de novo and salvage synthesis serves to maintain a reduced cellular environment and the tripeptide is a co-factor for many cytoplasmic enzymes and may also act as an important post-translational modification in a number of cellular proteins. The cysteine thiol acts as a nucleophile in reactions with both exogenous and endogenous electrophilic species. As a consequence, reactive oxygen species (ROS) are frequently targeted by GSH in both spontaneous and catalytic reactions. Since ROS have defined roles in cell signaling events as well as in human disease pathologies, an imbalance in expression of GSH and associated enzymes has been implicated in a variety of circumstances. Cause and effect links between GSH metabolism and diseases such as cancer, neurodegenerative diseases, cystic fibrosis (CF), HIV, and aging have been shown. Polymorphic expression of enzymes involved in GSH homeostasis influences susceptibility and progression of these conditions. See Danyelle M. Townsend, *, Kenneth D. Tew, Haim Tapiero Biomedicine & Pharmacotherapy 57 (2003) 145-155.

In various embodiments, the nanoparticles of the invention are administered orally. In an exemplary embodiment, the nanoparticles are administered at a dosage of from about 10 mg to about 100 mg per day, for example, from about 10 mg to about 50 mg per day.

In various embodiments of each of the methods of the invention, including the exemplary methods set forth above, the subject treated with the formulations of the invention is not in need of vitamin E supplementation. In various other embodiments, the metabolic parameter that is regulated or the disease that is treated by administration of the formulation is not a parameter or disease recognized as treatable or known to be ameliorated by vitamin E supplementation of the subject.

Art-accepted assays for alteration in blood chemistry or metabolism are of use to confirm the efficacy of therapeutically relevant (or other) dosages of the particles of the invention. The following provide examples illustrating just some of the conventional assays that can be used to analyze the efficacy of the present invention in varying dosages. Standard assays for cytokines, insulin, lipid peroxidation and vitamin C, CRP, MCP-1, IL-6, TNF-a, leptin, retinol binding protein and insulin levels in the plasma can take the form of the sandwich ELISA method using commercially available kits from Fisher Thermo Scientific Co, Rockford, Ill. Oxidative stress can be determined by measuring malondialdehyde (an end product of lipid peroxidation) by its reaction with thiobarbituric acid. See Jain, *J. Biol. Chem.* 264:21340-21345, 1989; Jain et al., *Diabetes* 38:1539-1543, 1989). Protein oxidation can be determined by the methods disclosed in Yan et al., *Arch. Biochem Biophys.* 327:330-334, 1996. Insulin resistance can for instance be determined by the HOMA method (Yaturu et al., *Cytokine* 34:219-23, 2006). Vitamin C concentration in the plasma can be determined by the method of Nino and Shaw. See Alan Wu (Ed). Teitz Clinical Guide to Laboratory Tests (Fourth Edition), Philadelphia, WB Saunders Co. 2006. Glycosylated hemoglobin can be determined using Glyco-Tek Affinity column kits and reagents (cat #5351) purchased from Helena Laboratories (Beaumont, Tex.). Glucose levels can be determined using glucose oxidase by Accucheck Advantage glucometer (Boehringer Manheim Corporation, Indianapolis, Ind.).

The following examples are given to illustrate the present invention. It should be understood, however, that the invention is not to be limited to the specific conditions or details described in these examples.

EXAMPLES

Example 1

Preparation of a Liquid Formulation Containing 1% Policosanol

1. Prepare a water solution (100 mL) containing sucrose laureate (0.1-0.5%) and warm up to 80-85° C. under stirring.
2. In a beaker, weigh the Policosanol (1 g) and at least one excipient or stabilizer (2-5 g) and warm up to 80-85° C. under stirring.
3. Pour the sugar ester solution into the beaker with Policosanol and the excipient under strong stirring and keep at 80-85° C. for 5 min under stirring. When the temperature is below 50° C., the formulation becomes transparent.
4. Switch off the heater and keep under moderate stirring until room temperature is reached.
5. Add a preservative (e.g., potassium sorbate, sodium benzoate, citric acid anhydrous).
6. Put the solution into the bottles.

Example 2

| Formulation having 1% Policosanol | |
|---|---|
| COMPONENT | % |
| Vitamin E TPGS | 4 |
| Policosanol | 1 |
| Sugar ester | 0.95 |
| Potassium sorbate | 0.12 |
| Sodium benzoate | 0.2 |
| Citric acid anhydrous | 0.1 |
| Water | 93.63 |

| Formulation having 2% Policosanol | |
|---|---|
| COMPONENT | % |
| Vitamin E TPGS | 6 |
| Policosanol | 2 |
| Sugar ester | 0.92 |
| Glycerin | 0.12 |
| Potassium sorbate | 0.12 |
| Sodium benzoate | 0.2 |
| Citric acid anhydrous | 0.1 |
| Water | 90.54 |

| Formulation having 3% Policosanol | |
|---|---|
| COMPONENT | % |
| Vitamin E TPGS | 8 |
| Policosanol | 3 |
| Sugar ester | 0.89 |
| Glycerin | 0.18 |
| Potassium sorbate | 0.12 |
| Sodium benzoate | 0.2 |
| Citric acid anhydrous | 0.1 |
| Water | 87.51 |

Example 3

Rat Studies Using 1% Solution of Policosanol (10 mg/mL) with a Particle Size of 53 nm and ~82-83% Octacosanol Materials and Methods Male Zucker Diabetic Fatty rats were purchased at 5 weeks of age from Charles River Laboratories. The animals were randomly numbered and housed individually in plastic colony cages in a climate controlled animal facility. The animals were cared for in accordance with and use of generally accepted Committee protocols. Rats were allowed 2 days for environmental and trainer handling acclimation. The rats were tested for hyperglycemia by measuring their blood glucose concentration. The blood glucose was measured by tail incision using an advantage Accu-Chek® glucometer (Boehringer Mannheim Corp., Indianapolis, Ind.). The rats were randomly divided into 3 groups. Each rat in the treatment group was supplemented with appropriate dose of a nanoparticulate policosanol formulation of the invention daily for 8 weeks by oral gavage using 20G feeding needles (Popper and Sons, New Hyde Park, N.Y.). The control group was supplemented with vehicle-buffer. Weight was monitored weekly to determine the policosanol supplementation dosage. The rats were maintained under standard housing conditions at 22±2° C. with 12:12-h light/dark cycles with a water and Purina 5008 lab chow diet ad libitum. At the end of 8 weeks, the rats were fasted overnight then euthanized for analysis by exposure to halothane (2-bromo-2-chloro-1,1,1-trifluoroethane). Blood was collected by puncturing the heart with a 19½ gauge needle and drawing the blood into a syringe containing heparin, then immediately transferring it to EDTA vacutainer tubes.

There were 3 groups of ZDF rats: 1. Controls-ZDF; 2. policosanol (5 mg per day/kg BW] supplemented ZDF, and (3) rats at the start of the supplementation. This provided us the baseline level of all the parameters to be analyzed in the blood of ZDF rats. Similar age Spraug Dawley rates were used as normal age-matched control rats kept on a normal diet.

Rats were maintained on Purina 5008 diet with and without policosanol for 8 weeks. Blood samples were collected into pre-cooled EDTA-tubes kept in an ice bucket. EDTA-blood was used for HbA1c, and CBC assays (done by the clinical hematology laboratory). EDTA-blood was centrifuged. RBC was used for GSH and lipid peroxidation assay. The clear plasma was saved for lipid peroxidation and protein oxidation products and for TNF-α, IL-6, MCP-1, CRP, adipokines, insulin sensitivity by ELISA assays. All analyses were performed immediately after blood collection. Samples for oxidative stress markers and pro-inflammatory cytokines were stored in a −70° C. freezer. Complete chemistry profiles (CMP2) including SGOT and SGPT levels were also done to reveal any signs of toxicity during policosanol supplementation. In cytokine assays, control sera samples were analyzed at all times to monitor the variation from plate to plate and on different days of cytokine analyses. Assays were repeated if the variation in control serum values from day to day was greater than 7%.

Cytokines, insulin, lipid peroxidation and vitamin C assays: CRP, MCP-1, IL-6, TNF-a, leptin, retinol binding protein and insulin levels in the plasma were determined by the sandwich ELISA method using commercially available kits from Fisher Thermo Scientific Co, Rockford, Ill.). All appropriate controls and standards as specified by the manufacturer's kit were used. In the cytokine assay, control samples were analyzed each time to check the variation from plate to plate on different days of analysis. Oxidative stress was determined by measuring malondialdehyde (an end product of lipid per oxidation) by its reaction with thiobarbituric acid (1, 2). See Jain "Hyperglycemia can cause membrane lipid peroxidation and osmotic fragility in human red blood cells." J Biol Chem 264:21340-21345, 1989; and Jain et al. "Erythrocyte membrane lipid peroxidation and glycosylated hemoglobin in diabetes" Diabetes 38:1539-1543, 1989. Protein oxidation was determined by the methods of Yan et al. in "Efficacy of hypochlorous acid scavengers in the prevention of protein carbonyl formation" Arch Biochem Biophys 327:330-334, 1996. Insulin resistance was determined by HOMA method. See Yaturu et al. "Resistin and adiponectin levels in subjects with coronary artery disease and type 2 diabetes." Cytokine 34:219-23, 2006; and Ismael et al. "Bockade of sensory abnormalities and kinin $B_1$ receptor expression by N-acetyl-L-cysteine and ramipril in a rat model of insulin resistance." Eur J. Pharmacol. 589:66-72, 2008. Vitamin C concentration in the plasma was determined by the method of Nino and Shaw. See Wu (ed). *Teitz Clinical Guide to Laboratory Tests* (Fourth Edition) Philadelphia, WB Saunders Co. 2006. GSH was determined by the method of Beutler in *Red Blood Cell Metabolism: A manual of Biochemical Methods* Pub: Grune and Stratton, N.Y. 131-134, 1984.

Measurement of Glycosylated Hemoglobin (GHb), Glucose and Insulin Resistance:

Glycosylated hemoglobin was determined using Glyco-Tek Affinity column kits and reagents (cat #5351) purchased from Helena Laboratories (Beaumont, Tex.). Glucose levels were determined using glucose oxidase by Accu-check Advantage glucometer (Boehringer Manheim Corporation, Indianapolis, Ind.).

Western blotting analyses of liver extracts: Tissues excised from the experimental rats were immediately frozen using liquid nitrogen and ground well into powders and frozen at −70° C. until further use. The frozen tissue powders (<150 mg) were washed by re-suspending in 1 mL of PBS containing protease inhibitors, mildly vortexed and centrifuged at 15,000 rpm at 4° C. for 10 min. The supernatants were discarded and the cell pellets were washed once more as mentioned above and then resuspended in 500 (mL of extraction buffer (25 mM Tris, 0.5 mM EDTA, PMSF 0.1 mM, pH 7.4) with protease inhibitors and homogenized using homogenizer and subjected to mild sonication. The tubes were centrifuged at 15,000 rpm (4° C., 30 min) and the supernatants (extracts) were collected. The collected extracts were subjected to centrifugation once more as described above and removed of cell debris. The protein content of the extracts was estimated using the BCA protein assay. Equal amounts of proteins from each group were loaded onto an SDS-polyacrylamide gel after boiling for 5 minutes with mercaptoethanol as reducing agent. The separated proteins were transferred to a nitrocellulose membrane, blocked with 1% BSA in T-PBS and incubated overnight at 4° C. with the respective primary antibodies. The next day, membranes were washed with T-PBS (8 minutes, 4 cycles) and incubated with secondary antibodies in 5% non-fat milk for 30 min. at room temperature. The membranes were again washed with T-PBS (8 minutes, 4 cycles), treated with chemiluminescence reagents for 2 minutes and exposed to X-ray films, which are developed through autoradiography.

All chemicals were purchased from Sigma Chemical Co. (St. Louis, Mo.) unless otherwise mentioned.

Data analysis: Data was analyzed using ANOVA between different groups with Sigma Plot statistical software (Jandel Scientific, San Rafael, Calif.). A p value of less than 0.05 was considered significant.

Results

No difference was observed in the body weight at the time of sacrifice between different treatment groups. The weekly intake of diet by each rat, as assessed at 5 and 7 weeks after start of supplementation, was similar in both the groups. The body weight and food intake for the male Zucker-Fatty rats supplemented with policosanol for 8 weeks are provided in Table 1 below. Each value represents the mean±SE.

TABLE I

| entry | N units | Body Weight @ Sacrifice g | Food Intake 5 wks g/day | Food Intake 7 wks g/day |
|---|---|---|---|---|
| Normal (SD) | 6 | 439.00 ± 7.35 | 26.90 ± .67 | 27.43 ± 1.02 |
| Diabetic | 7 | 370.57 ± 3.92 | 37.86 ± 0.73 | 38.18 ± 1.17 |
| 5 mg/kilo policosanol | 5 | 368.80 ± 6.62 | 34.23 ± 2.28 | 37.94 ± 1.84 |

In all the figures, values marked '*' are statistically significant compared with controls (p<0.05). FIG. 30 provides data on alanine aminotransferase (ALT), alkaline phosphatase (AP), aspartate aminotransferase (AST), blood urea nitrogen (BUN), creatinine and anion Gap levels in the blood of supplemented rats. Analysis of results demonstrate that policosanol supplementation lowered blood levels of glucose, total cholesterol, triglycerides, protein oxidation, MCP-1 and CRP and alkaline phosphatase, and increased blood levels of vitamin C. While policosanol did not change blood levels of transaminases, it did lower alkaline phosphatase levels compared with diabetic rats.

Table II shows that policosanol supplementation did not affect hemoglobin, hematocrit or RBC counts in diabetic rats, which rules out any effect of altered red cell survival on lower glycosylated hemoglobin levels in policosanol supplemented ZDF rats and affirm lack of any sign of toxicity in policosanol supplemented rats. The data demonstrates that policosanol supplementation does not appear to cause any toxicity as assessed by liver function or renal function tests.

TABLE II

Effects of policosanol on blood hemoglobin, hematocrit, and red blood cell counts in Zucker Fatty Rats. Each value represents the mean ± SE

| entry | N units | RBC $10^6/\mu L$ | Hemoglobin g/dL | Hematocrit % |
|---|---|---|---|---|
| Normal (SD) | 6 | 7.99 ± 0.13 | 15.27 ± 0.20 | 44.48 ± 0.61 |
| Diabetic | 7 | 9.48 ± 0.13 | 15.96 ± 0.23 | 48.54 ± 0.78 |
| 5 mg/kilo policosanol | 5 | 8.50 ± 0.23 | 14.46 ± 0.43 | 43.34 ± 1.23 |

The liver plays a major role in the regulation of glucose metabolism. See Michael et al. "Loss of Insulin signaling in hepatocytes leads to severe insulin resistance and progressive hepatic dysfunction." Mol. Cell. 6:87-97, 2000. The liver is a storage organ for glucose, proteins and vitamins. The glycogenic and gluconeogenic pathways which are major regulators of blood glucose levels are unique to liver. Several hormones, including insulin, glucagon, growth hormone, cortisol, and catecholamines contribute to the regulation of glucose metabolism by the liver. Therefore we examined the role of NFkB activation in liver and its potential contribution on glucose metabolism in policosanol supplemented rats.

Figure 27:
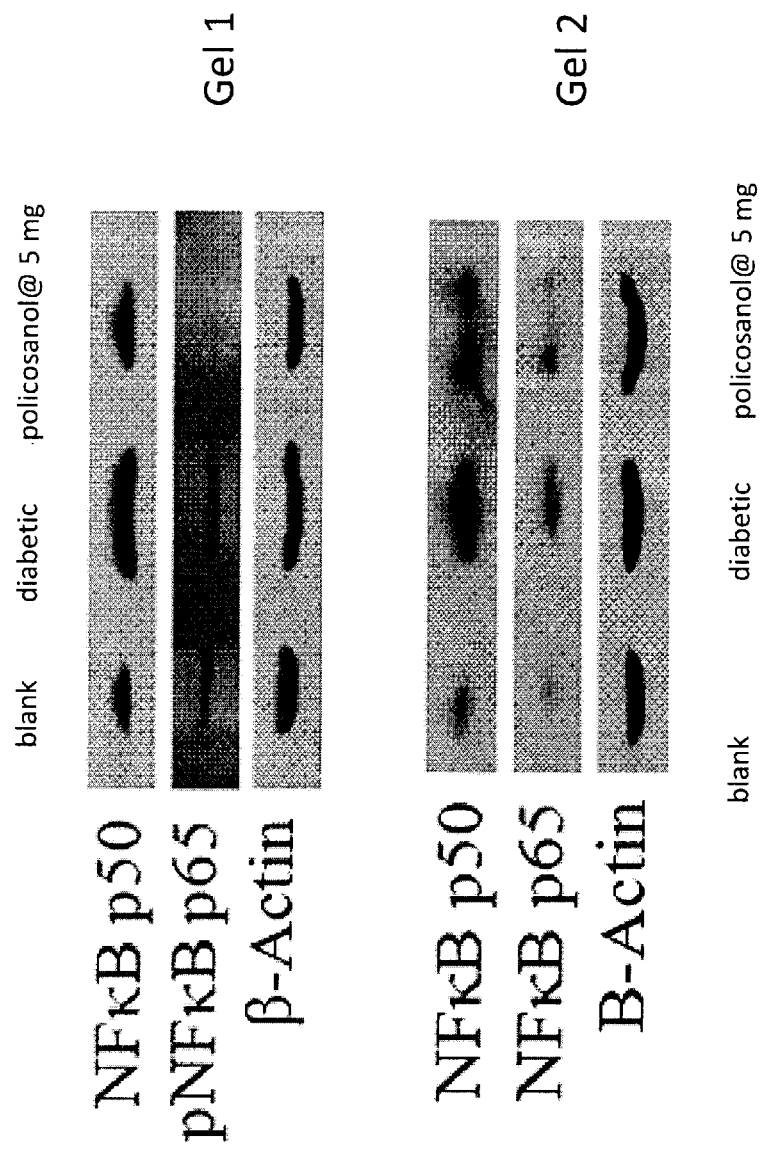
FIG. 27 shows NF-KB (nuclear factor kappa-light-chain-enhancer of activated B cells) p50 and p65 protein intensities by western blot analysis in untreated rats and rats treated with particles of the invention.
Figure 28:
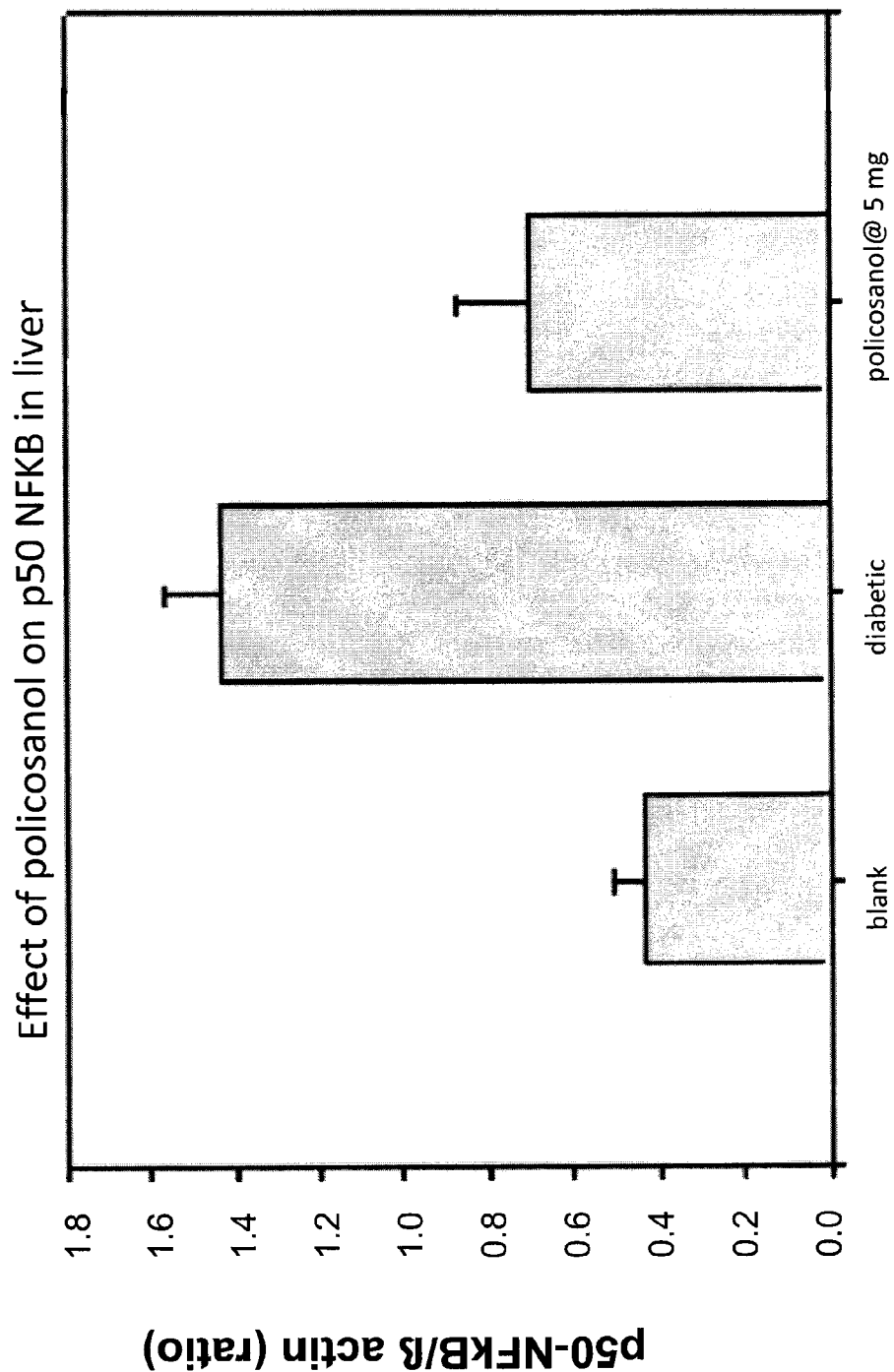
FIG. 28 shows p-50-nf-kb/beta actin ratio in untreated rats and rats treated with particles of the invention.
Figure 29:
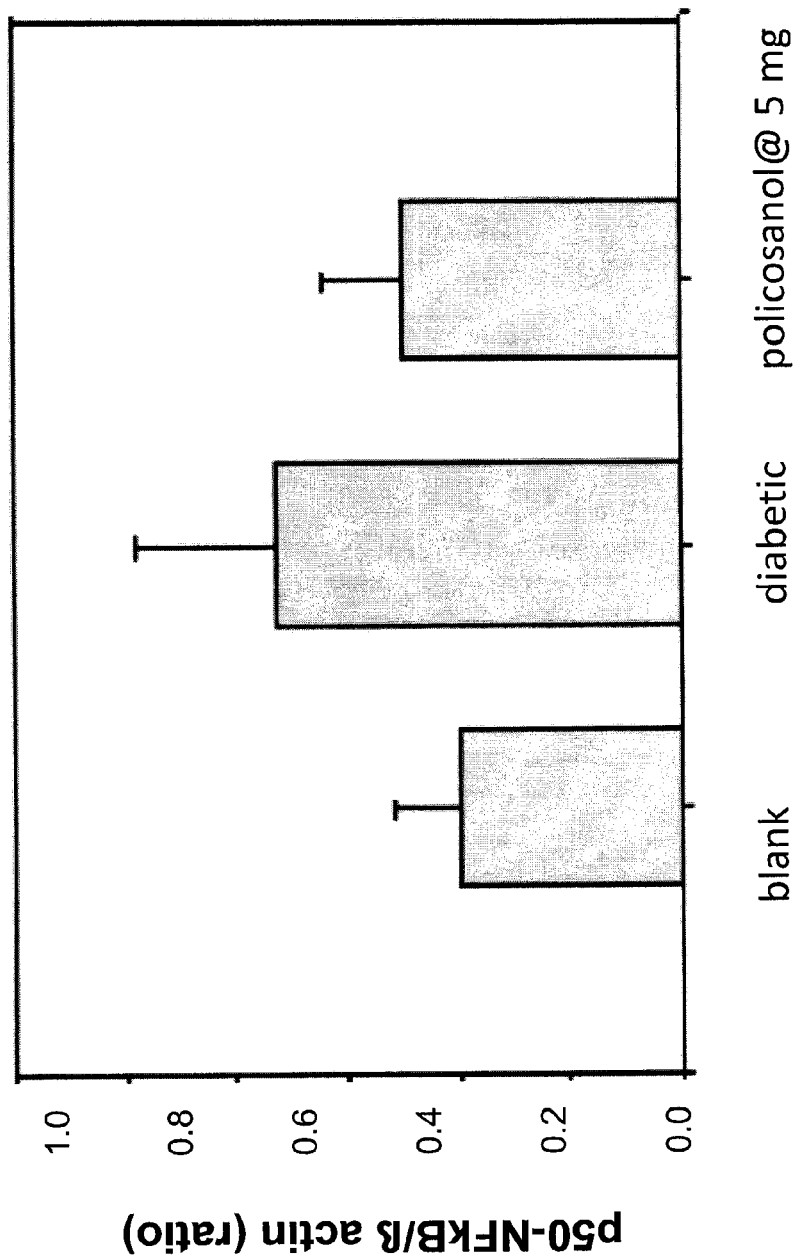
FIG. 29 shows p-50-nf-kb/beta actin ratio in untreated rats and rats treated with particles of the invention.

The results of our study show that experimental diabetes induced the activation of NFkB in the livers of diabetic Zucker rats when compared to baseline controls. See Yerneni et al. "Hyperglycemia-induced activation of nuclear transcription factor kappaB in vascular smooth muscle cells." Diabetes. 48:855-64, 1999. NFkB is a known target for hyperglycemia. See Meng et al. "Akt is a downstream target of NFkB." J Biol Chem 277: 29674-29680. Oxidative stress associated with diabetes is a known activator of NFkB, a heterodimer consisting of two DNA-binding subunits known as p50 and p65. NFkB is present in the cytoplasm complexed to its inhibitory protein known as inhibitory kB (IkB). Following activation, IkB dissociates from NFkB and undergoes ubiquitination and degradation. NFkB is freed to undergo nuclear translocation. Upon its nuclear translocation, NFkB undergoes serine phosphorylation at residue 276 in its p65 subunit and associates with surrounding chromatin components. It subsequently binds with DNA and promotes the transcription of pro-inflammotory cytokines and known mediator of insulin resistance. Therefore, measurement of the phosphorylated p65 subunit of NFkB is an effective tool for determining NFkB activation. As shown in FIG. 27, the diabetic rats exhibited elevated NFkB activation. We also found that NFkB was inhibited by administration of the policosanol formulation described herein. Our results show that policosanol supplementation resulted in a significant improvement in glycemia and inhibition of oxidative stress and secretion of pro-inflammatory cytokines in diabetic rats.

In conclusion, policosanol supplementation has the potential to lower blood levels of glycemia and the pro-inflammatory cytokines and increase in vitamin C levels. This effect is mediated by inhibition of NFkB activation by policosanol.

Example 4

Clinical Trial Study

The 1% policosanol formulation described above was used in an open label single center study to evaluate the effectiveness and tolerability at lowering blood pressure, in diabetic patients as the primary end point and evaluating other key biomarkers. The results of the study are summarized below in example 4.1.

Example 4.1

Homa % B (beta cell function (% B) and insulin sensitivity (% S), and Insulin resistance were calculated using HOMA Calculator v2.2.2 (Diabetes Care 1998; 21: 2191-92). The study involved 14 diabetic subjects with an average age of 48+ or −22 years. Average duration of diabetes was 13.5+ or −12.5 years. Subjects took 20 mgs (1 mL twice ea day) for 12 weeks. There were no controls on the subjects' diets.

As shown in Table III below, the systolic and diastolic blood pressures, C-reactive protein levels, very low-density lipid levels (VLDL), serum albumin, serum globulin levels, and waist loss in patients with BMI greater than 28 were statistically significant with p<<0.05. The results show that it can be useful in treating hypertension, reducing cardiovascular risk in patients with high C-reactive protein levels and reducing VLDL (a precursor of LDL) reducing waist circumference, and improving kidney function. The policosanol was extremely well tolerated and no adverse events were reported by the patients.

TABLE III

| Entry | N | average value at baseline | standard deviation | average value at 12 weeks | standard deviation | % change | p value |
|---|---|---|---|---|---|---|---|
| Waist circumference (cms) BMI over 28 | 4 | 110.25 | 13.07 | 98.75 | 17.73 | −10.4 | 0.0002 |
| serum albumin (g/dl) | 14 | 4.4 | 0.28 | 3.82 | 0.37 | −13.1 | 0.0003 |
| systolic blood pressure (mm) | 14 | 141.71 | 22.94 | 121.07 | 12.16 | −14.5 | 0.00074 |
| albumin/globulin ratio | 14 | 1.50 | 0.33 | 1.23 | 0.31 | −16.6 | 0.003 |
| serum globulin (g/dl) | 14 | 2.66 | 0.32 | 3.10 | 0.50 | 16.5 | 0.01 |
| VLDl (very low density lipids) (mg/dl) | 14 | 70.5 | 25.44 | 45.21 | 19.04 | −49.2 | 0.0118 |
| diastolic blood pressure (mm) | 14 | 87.35 | 13.14 | 75.71 | 8.69 | −12.98 | 0.0279 |
| Hs-CRP (C-reactive protein) mg/L | 14 | 3.63 | 2.66 | 2.02 | 1.42 | −35.8 | 0.05 |
| fasting insulin (mU/L) | 14 | 15.07 | 8.80 | 11.77 | 5.31 | −28.5 | 0.20 |
| insulin resistance | 14 | 2.6 | 2.13 | 1.9 | 0.84 | −26.9 | 0.21 |
| SGPT (U/L) | 14 | 29.35 | 17.62 | 21.75 | 9.63 | −26.06 | 0.26 |
| Waist circumference (cms) | 14 | 96.35 | 12.82 | 91.28 | 12.25 | −5.26 | 0.31 |
| vitamin C (mg %) | 14 | 0.29 | 0.08 | 0.35 | 0.17 | 20.6 | 0.31 |
| Homa % S | 14 | 59.16 | 27.87 | 64.62 | 24.22 | 9.3 | 0.33 |
| cholesterol/hdl ratio | 14 | 4.87 | 1.00 | 4.60 | 1.02 | −5.27 | 0.35 |
| Waist hip ratio | 14 | 0.95 | 0.075 | 0.93 | 0.086 | −2.1 | 0.38 |
| fasting glucose (mg %) | 13 | 194.07 | 53.2 | 181.69 | 63.9 | −6.36 | 0.38 |
| SGOT U/L) | 14 | 22.1 | 9.49 | 19 | 5.05 | −16.8 | 0.43 |
| Hdl (mg/dl) | 14 | 39.78 | 7.47 | 40.78 | 7.36 | 2.5 | 0.45 |
| total cholesterol (mg/dl) | 14 | 191 | 37.46 | 181.29 | 33.03 | −5.03 | 0.47 |
| Hip (cms) | 14 | 100.42 | 17.32 | 97.71 | 16.32 | −2.8 | 0.48 |
| Homa % B | 14 | 41.5 | 22.1 | 48.5 | 5.05 | 16.8 | 0.58 |
| Triglycerides (mg/dl) | 14 | 208.78 | 137 | 191.50 | 105 | −8.2 | 0.71 |

TABLE III-continued

| Entry | N | average value at baseline | standard deviation | average value at 12 weeks | standard deviation | % change | p value |
|---|---|---|---|---|---|---|---|
| HbA1c % (glycosylated hemoglobin) | 14 | 9.54 | 1.87 | 9.29 | 2.27 | −2.6 | 0.80 |
| Weight (lbs) | 14 | 148.50 | 17.3 | 146.74 | 16.2 | −0.1 | 0.99 |

Based on the highly significant results in lowering systolic pressure in diabetes patients, one can calculate reduction in risk factors based on the UK Prospective Diabetes Study (UKPDS). This 10-year study of 5000 patients concluded that there is a direct risk relationship between complication of diabetes and systolic blood pressure. A 10 mm drop in systolic pressure reduces risk factors by 10-20%. This is shown in Table IV below. See "Systolic pressure lowers the risk of association of systolic blood pressure with macro-vascular and micro vascular complications of Type 2 diabetes: prospective observational study"*British Medical Journal* (2000) 321: 412-419.

TABLE IV

UKPDS Summary

| Entry | % Risk reduction based systolic pressure reduction |
|---|---|
| Any diabetes related end point | 12 |
| Diabetes related deaths | 17 |
| All cause mortality | 12 |
| Fatal and non fatal myocardial infraction | 12 |
| Fatal and non fatal stroke | 19 |
| Micro vascular endpoints | 13 |
| Amputation or death from peripheral heart disease | 16 |
| Heart failure | 17 |

TABLE V

Results based on our human study.

| Entry | % Risk reduction based on systolic pressure reduction |
|---|---|
| Any diabetes related end point | 33 |
| Diabetes related deaths | 47 |
| All cause mortality | 33 |
| Fatal and non fatal myocardial infraction | 33 |
| Fatal and non fatal stroke | 19 |
| Micro vascular endpoints | 36 |
| Amputation or death from peripheral heart disease | 44 |
| Heart failure | 33 |

Applying the UKPDS risk assessment methodology, it is clear that at 12 weeks, the risk reductions were substantial. One can infer that the policosanol formulation of the invention is useful in mitigating risk factors in diabetes patients and those at risk from hypertension related diseases.

Example 4.2

The 1% policosanol formulation described herein (20 mg per day) was given to a 26-year-old male diagnosed at age 3 with type 1 diabetes. His daily insulin intake before treatment was 30 units every day. The fasting insulin was measured at baseline and over 21 weeks. The results are shown in Table VI below.

TABLE VI

| Week | Fasting insulin levels (mU/L) |
|---|---|
| 0 | 0.19 |
| 3 | 0.33 |
| 6 | 0.45 |
| 12 | 31.75 |
| 15 | 16 |
| 18 | 22 |
| 21 | 16.6 |

Based on the above data, the policosanol formulation could be helpful in type 1-diabetes patients in enhancing the beta cell activity in increasing endogenous insulin production.

Example 4.3

A 4-year-old girl diagnosed with nephrotic syndrome was treated with the 1% policosanol formulation described herein at 10 mg per day. Nephrotic syndrome is a group of symptoms including protein in the urine (more than 3.5 grams per day) low blood protein levels, high cholesterol levels, and swelling. It is caused by various disorders that damage the kidneys, particularly the basement membrane of the glomerulus. This immediately causes abnormal excretion of protein in the urine. Nephrotic syndrome can affect all age groups. In children, it is most common from age 2 to 6.

At base line, there were no urinary tract symptoms. Her urine to protein creatinine ratio (UPCR) was 6.0. After treatment with the policosanol formulation for 2 weeks, the UPCR ratio decreased to 1.6 and after 4 weeks to 0.6. Based on the data below, the poliosanol formulation could be useful in treating kidney diseases as shown in example 4.1 where reduction of albumin was statistically significant.

| | UPCR ratio |
|---|---|
| Baseline | 6 |
| after 2 weeks | 1.6 |
| after 4 weeks | 0.6 |

Example 4.4

A 48 year old male with symptoms of knee and joint pain during the day and numbness and pain at night in the joints was treated with the 1% policosanol formulation described herein at 20 mg per day for 3 months. Blood plasma levels of vitamin C at base line was low (at about 0.15 mg %) despite adequate consumption of vitamin C through diet. Rheumatoid arthritis and osteoarthritis were ruled out by X-ray and MRI. RA factor and uric acid levels were normal.

|  | plasma vitamin C mg % |
| --- | --- |
| base line | 0.15 |
| after 3 months | 0.64 |

Percent increase = 326

The patient's knee and joint pain during daytime was completely suppressed and his night time pain reduced to a minimum.

Example 4.5

A 43 year old, male type 2 diabetes patient (detected at age 38) had very low levels of plasma Vitamin C at base line of 0.27 mg %. For this study, he was given the 1% policosanol formulation described herein at 20 mg per day for six months.

At the end of six months, his plasma vitamin C levels had improved to 3.82 mg %. Improvement in HbA1c and fasting insulin levels were also observed.

|  | vitamin C mg % | fasting insulin mg/l | hs-C reactive protein mg/L | hb1ac % |
| --- | --- | --- | --- | --- |
| Baseline | 0.27 | 11.79 | 3.9 | 7.4 |
| at 6 months | 3.82 | 5.67 | 0.87 | 6.2 |

Example 4.6

A 42 year old male diagnosed with type II diabetes and hyperinsulinemia (diagnosed at age 37) was treated with the 1% policosanol formulation described herein at 20 mg per day for 6 months. As shown in the table below, he demonstrated a significant reduction in his levels of fasting insulin at the end of six months.

|  | fasting insulin mg/l |
| --- | --- |
| Baseline | 34.38 |
| at 6 months | 4.59 |

Example 4.7

A 47 year old female patient who was diagnosed with type 2 diabetes at age 41 was treated with the 1% policosanol formulation described herein at 20 mg per day for 6 months. At the end of six months, significant reductions in waist hip ratio, fasting glucose levels, and hs-C reactive protein levels were observed.

|  | waist hip ratio | fasting glucose mg/l | hs-C reactive protein mg/L |
| --- | --- | --- | --- |
| Baseline | 0.98 | 292 | 8.74 |
| at 6 months | 0.77 | 182 | 3.4 |

Example 4.8

A 48 year old, obese (BMI>30) male patient, non-diabetic, with very low HDL at base line was treated with the 1% policosanol formulation described herein at 40 mg per day for 8 weeks. The results indicated vastly improved HDL, LDL, CHOL/HDL (total cholesterol/HDL) ratios and a 6 kg reduction in weight and improvement in BMI ratio.

|  | Total Cholesterol mg/dl | HDL mg/dl | LDL mg/dl | Triglyceride | VLDL mg/dl | CHOL/HDL ratio | BMI |
| --- | --- | --- | --- | --- | --- | --- | --- |
| Baseline | 200 | 24 | 120 | 278 | 55.6 | 8.33 | 30.3 |
| @ 8 weeks | 183 | 55 | 76 | 258 | 51.6 | 3.32 | 28.3 |
| % change | −8.5 | 129 | −36.6 | −7.2 | −7.1 | −60 | −6.6 |

Example 4.9

A 50 year old female diagnosed with hypertension and type 2 diabetes was treated with the 1% policosanol formulation described herein at 20 mg per day. The results indicated vastly improved blood pressure at 6 months.

|  | systolic pressure mm of Hg | diastolic pressure in mm of Hg |
| --- | --- | --- |
| Base line | 183 | 112 |
| at 6 months | 130 | 80 |

Example 4.10

A ten year old girl was diagnosed with kidney infection with albumin in the urine. She was treated with the 1% policosanol formulation described herein @ 10 mg per day. Urine test after 10 days showed complete remission of infection and no traces of albumin in the urine. The results demonstrate the present invention's usefulness in treating kidney infection that exhibits the presence of albumin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising nanoparticles of policosanol, wherein each nanoparticle comprises:
   (a) a policosanol fraction comprising about 70% to 90% octacosanol; and
   (b) a stabilizer fraction comprising tocopheryl polyethylene glycol (1000) succinate ("TPGS"),
   wherein the ratio of octacosanol:stabilizer fraction ranges from about 1:1.6 to about 1:2.8 and the nanoparticles have a size between about 40 nm and about 100 nm in diameter and wherein at least 99% of the nanoparticles have a particle size of less than about 70 nm as determined by a light scattering method.

2. The composition of claim 1, wherein said policosanol fraction further comprises triacontanol.

3. The composition of claim 2, wherein said nanoparticle has a ratio of octacosanol:triacontanol of from about 9:1 to about 15:1.

4. The composition of claim 2, wherein said nanoparticle has a ratio of octacosanol:hexacosanol of from about 16:1 to about 20:1.

5. The composition of claim 1, wherein said nanoparticle has a size of about 60 nm in diameter.

6. The composition of claim 1, further comprising a pharmaceutically acceptable carrier.

7. The composition of claim 6, said composition being a unit dosage formulation comprising from about 10 to about 30 mg/mL (wt/vol) of said nanoparticles.

8. The composition of claim 1, further comprising a sugar ester, potassium sorbate, sodium benzoate, anhydrous citric acid, and water.

9. The composition of claim 1, wherein said composition comprises vitamin E TPGS in a concentration of 4%-8%.

10. The composition of claim 1, wherein said composition comprises policosanol in a concentration of 1-3%.

11. A method of increasing serum vitamin C levels in a subject comprising: administering to said subject the composition of claim 6 in an amount effective to increase said serum vitamin C levels in the subject.

12. A method of inhibiting NF-κB protein level in a subject, said method comprising: administering to said subject the composition of claim 6 in an amount effective to inhibit the activation of NF-Kb level in the subject.

13. A method of increasing adiponectin levels in a subject, said method comprising: administering to said subject the composition of claim 6 in an amount effective to increase said adiponectin levels in the subject.

14. A method of reducing TNF alpha level in a subject, said method comprising: administering to said subject the composition of claim 6 in an amount effective to reduce said TNF alpha level in the subject.

* * * * *